US011980563B2

(12) United States Patent
Zelik et al.

(10) Patent No.: US 11,980,563 B2
(45) Date of Patent: May 14, 2024

(54) WEARABLE ASSISTANCE DEVICES AND METHODS OF OPERATION

(71) Applicant: VANDERBILT UNIVERSITY, Nashville, TN (US)

(72) Inventors: Karl Zelik, Nashville, TN (US); Matthew Yandell, Nashville, TN (US); Dustin Howser, Bristol, TN (US); Erik Lamers, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/478,310

(22) PCT Filed: Jan. 19, 2018

(86) PCT No.: PCT/US2018/014393
§ 371 (c)(1),
(2) Date: Jul. 16, 2019

(87) PCT Pub. No.: WO2018/136722
PCT Pub. Date: Jul. 26, 2018

(65) Prior Publication Data
US 2019/0358074 A1 Nov. 28, 2019

Related U.S. Application Data

(60) Provisional application No. 62/448,104, filed on Jan. 19, 2017.

(51) Int. Cl.
*A61F 5/02* (2006.01)
*F16D 13/58* (2006.01)
(Continued)

(52) U.S. Cl.
CPC .............. *A61F 5/028* (2013.01); *A61F 5/026* (2013.01); *F16D 13/58* (2013.01); *A61B 5/389* (2021.01); *A61F 2005/0197* (2013.01)

(58) Field of Classification Search
CPC .. A61F 5/02; A61F 5/026; A61F 5/028; A61F 5/03; A61F 5/30; A61F 13/148;
(Continued)

(56) References Cited

U.S. PATENT DOCUMENTS

| 330,213 | A | * | 11/1885 | Deweese | ................. | A01K 1/04 |
| | | | | | | 54/34 |
| 596,839 | A | | 1/1898 | Bassett | | |

(Continued)

FOREIGN PATENT DOCUMENTS

| DE | 10 2004 009 315 A1 | 9/2005 |
| DE | 202005011650 U1 | 12/2006 |

(Continued)

OTHER PUBLICATIONS

International Search Report for International Application No. PCT/US2018/014393, dated May 17, 2018 (2 pages).

(Continued)

*Primary Examiner* — Ophelia A Hawthorne
*Assistant Examiner* — Michael Milo
(74) *Attorney, Agent, or Firm* — BLANK ROME LLP

(57) ABSTRACT

Wearable assistance devices and methods of operating the same are provided. A wearable assistance device includes an upper-body interface with a front side and a rear side and a lower-body interface with a front side and a rear side. The assistance device also includes one or more elastic members, each of the elastic members mechanically coupling the upper-body interface to the lower-body interface and extending from the rear side of the upper-body interface to the rear side of the lower-body interface and along a back of the user so as to provide an assistive force parallel to the back of the user. Further, the assistance device also includes a clutch mechanism associated with each one of the elastic members, the clutch mechanism configured for selectively (Continued)

adjusting the assistive force provided by the one of the elastic members.

33 Claims, 27 Drawing Sheets

(51) Int. Cl.
*A61B 5/389* (2021.01)
*A61F 5/01* (2006.01)

(58) Field of Classification Search
CPC ....... A61F 13/00038; A61F 2005/0197; A61B 5/389; A61H 2201/1602; A61H 2003/0283; A61H 2201/1623; A41C 1/08; F16D 13/58
USPC .... 602/19, 24; 128/869, 870, 874, 875, 876, 128/882
See application file for complete search history.

(56) References Cited

U.S. PATENT DOCUMENTS

| | | | |
|---|---|---|---|
| 1,098,492 A | | 6/1914 | Gibson |
| 1,386,067 A | | 8/1921 | Mason |
| 1,553,874 A | * | 9/1925 | Nivens ...................... A61F 5/02 2/44 |
| 4,709,692 A | | 12/1987 | Kirschenberg |
| 5,256,135 A | | 10/1993 | Avihod |
| 5,709,648 A | | 1/1998 | Webb |
| 5,716,307 A | * | 2/1998 | Vadher ............... A63B 21/4043 482/125 |
| 5,743,866 A | | 4/1998 | Bauerfeind et al. |
| 5,816,251 A | * | 10/1998 | Glisan .................... A61F 5/026 128/845 |
| 6,129,691 A | | 10/2000 | Ruppert |
| 6,190,342 B1 | | 2/2001 | Taylor |
| 6,450,131 B1 | | 9/2002 | Broman |
| 7,553,266 B2 | | 6/2009 | Abdoli-Eramaki |
| 8,241,090 B2 | | 8/2012 | Michael |
| 8,568,344 B2 | | 10/2013 | Ferguson |
| 8,832,863 B2 | * | 9/2014 | Yang .................. A41D 13/0015 2/69 |
| 9,682,005 B2 | | 6/2017 | Herr |
| 10,166,679 B2 | | 1/2019 | Tanibayashi |
| 10,463,562 B2 | | 11/2019 | Chavarria |
| 10,588,771 B2 | | 3/2020 | Holscher et al. |
| 2005/0130815 A1 | * | 6/2005 | Abdoli-Eramaki ...... A61H 3/00 482/121 |
| 2005/0263990 A1 | * | 12/2005 | Clute ...................... B60R 21/18 280/733 |
| 2007/0045570 A1 | | 1/2007 | Afanasenko et al. |
| 2009/0118655 A1 | | 5/2009 | Wang |
| 2010/0125230 A1 | | 5/2010 | Hurley |
| 2010/0204630 A1 | | 8/2010 | Sandifer et al. |
| 2012/0130293 A1 | | 5/2012 | Brown |
| 2012/0184881 A1 | | 7/2012 | Kobayashi et al. |
| 2013/0006386 A1 | * | 1/2013 | Hansen ................. A61F 2/6607 623/47 |
| 2013/0160189 A1 | | 6/2013 | Yang |
| 2013/0211295 A1 | | 8/2013 | Johnson et al. |
| 2013/0296746 A1 | * | 11/2013 | Herr ................... A63B 23/0405 601/34 |
| 2014/0100501 A1 | | 4/2014 | Burke et al. |
| 2014/0135674 A1 | | 5/2014 | Kirk |
| 2014/0277739 A1 | * | 9/2014 | Kornbluh ................ F16D 28/00 29/428 |
| 2015/0133842 A1 | | 5/2015 | Ferrigolo |
| 2015/0359698 A1 | | 12/2015 | Popovic et al. |
| 2016/0107309 A1 | | 4/2016 | Walsh et al. |
| 2016/0193067 A1 | | 7/2016 | Petursson et al. |
| 2016/0220438 A1 | | 8/2016 | Walsh et al. |
| 2016/0250062 A1 | | 9/2016 | Radaelli |
| 2017/0209330 A1 | | 7/2017 | Hughes et al. |
| 2017/0232617 A1 | | 8/2017 | Tanibayashi et al. |
| 2018/0093374 A1 | | 4/2018 | Holgate |
| 2018/0193686 A1 | | 7/2018 | Adeeko, Jr. |
| 2018/0221189 A1 | | 8/2018 | Garth et al. |
| 2019/0015235 A1 | | 1/2019 | Badger |
| 2019/0231574 A1 | | 8/2019 | Kazerooni |
| 2019/0358074 A1 | | 11/2019 | Zelik et al. |
| 2019/0380904 A1 | | 12/2019 | Panizzolo et al. |
| 2020/0038219 A1 | | 2/2020 | Mizera et al. |

FOREIGN PATENT DOCUMENTS

| | | | | |
|---|---|---|---|---|
| DE | 102015208125 A1 | * | 11/2016 | ............... A61F 5/02 |
| JP | 2008067762 A | * | 3/2008 | ........... A61F 5/0102 |
| JP | 2013 144858 A | | 7/2013 | |
| JP | 2016 083254 A | | 5/2016 | |
| KR | 1020160031603 A | | 3/2016 | |
| KR | 20170005173 A | | 1/2017 | |
| WO | WO 2005/056124 A1 | | 6/2005 | |
| WO | WO 2018/122100 A1 | | 7/2010 | |
| WO | WO 2015/088863 A2 | | 6/2015 | |
| WO | WO-2015157731 A1 | * | 10/2015 | ........... A61F 5/0102 |
| WO | 2017173441 A1 | | 10/2017 | |
| WO | WO 2018/067363 A1 | | 4/2018 | |
| WO | 2018122106 A1 | | 7/2018 | |
| WO | WO 2018/136722 A1 | | 7/2018 | |
| WO | WO 2019/161232 A1 | | 8/2019 | |

OTHER PUBLICATIONS

International Preliminary Report on Patentability for International Application No. PCT/US2018/014393, dated Jul. 23, 2019 (8 pages).
Written Opinion of the International Searching Authority for International Application No. PCT/US2018/014393 dated May 17, 2018.
ISB Poster Final EPL, (CREATE) Mar. 2016 (Mar. 2016); retrieved from the internet Apr. 19, 2019; https://s3.amazonaws.com/vu-my/wp-content/uploads/sites/1409/2016/03/31171620/ISB-Poster-Final-EPL.pdf., "How It's Controlled," Middle Figure and Assistive Garment Prototype Figure.
Nasiri et al., "Reducing the Energy Cost of Human Running Using an Unpowered Exoskeleton", IEEE Transactions on Neural Systems and Rehabilitation Engineering, vol. 26, No. 10, Oct. 2018, pp. 2026-2032.
Simpson et al., "Connecting the legs with a spring improves human running economy", Journal of Experimental Biology, 2019, pp. 1-10.
Chaichaowarat et al., "Passive Knee Exoskeleton Using Torsion Spring for Cycling Assistance", IEEE, 2017, pp. 3069-3074.
Ranaweera et al., "Development of a Passively Powered Knee Exoskeleton for Squat Lifting", Journal of Robotics, Networking and Artificial Life, vol. 5, No. 1, 2018, pp. 45-51.
Rogers et al., "A Quasi-Passive Knee Exoskeleton to Assist During Descent", 2017, pp. 63-67.
Sridar et al., "Development of a Soft Inflatable Exosuit for Knee Rehabilitation", 2017 IEEE/RSJ (IROS), pp. 3722-3727.
Elliott et al., "Design of a Clutch-Spring Knee Exoskeleton for Running", Journal of Medical Devices, 2014, vol. 8, pp. 1-11.
Lamers, "Modeling, Design and Evaluation of a New Extensible Moment Arm Mechanism to Improve Exosuit Comfort and Performance", pp. 1-21.
International Search Report of International Application No. PCT/US21/37579.
Extended European Search Report dated Dec. 23, 2022 from corresponding EP Application No. 20813296.9.
International Search Report and Written Opinion from PCT/US2021/022531 dated Jun. 3, 2021.
Yumeko Imamura et al: "Motion-based design of elastic belts for passive assistive device using musculoskeletal model", Robotics and Biomimetics (ROBIO), 2011 IEEE International Conference on, IEEE, Dec. 7, 2011 (Dec. 7, 2011), pp. 1343-1348, XP032165973, DOI: 10.1109/ROBI0.2011.6181475 ISBN: 978-1-4577-2136-6.
Communication pursuant to Article 94(3) EPC dated Jul. 8, 2022 from corresponding EP Application No. 18 741 272.1.

(56) References Cited

OTHER PUBLICATIONS

Extended European Search Report dated Jun. 1, 2023, issued in a related EP application No. 20814224.0.
International Search Report and Written Opinion, mail date Nov. 28, 2023, 19 pages, received in PCT application No. PCT/2023/US066231.
European Search Report received in corresponding patent application No. 21772646.2, issued Mar. 19, 2024.

* cited by examiner

600

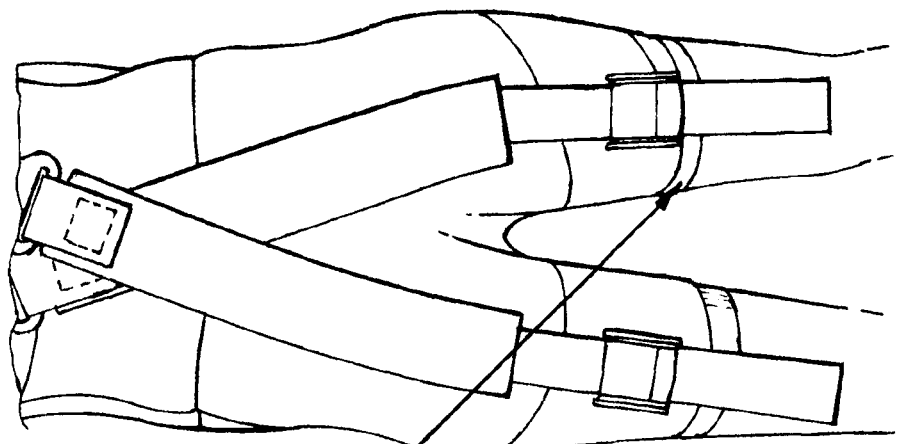

SUMMARY OF HOW IT WORKS

1. SILICONE OR THERMOPLASTIC ELASTOMER SLEEVE CONFORMS AROUND LIMB SECTION AND GRIPS THE SKIN TO PREVENT SLIPPING.
2. FABRIC OUTER ATTACHES ON TOP OF LINER (VIA VELCRO OR OTHER MEANS).
3. EXTERNAL FORCE FROM EXO ELASTIC BANDS CAN THEN BE APPLIED TO THE OUTER COVER.
4. FORCE IS DISTRIBUTED OVER SURFACE AREA OF SKIN ENABLING LARGER FORCES TO BE APPLIED WITHOUT SLIPPING.

FIG. 23

WEARABLE ASSISTANCE DEVICES AND METHODS OF OPERATION

CROSS-REFERENCE TO RELATED APPLICATIONS

This application is a National Phase of International Application No: PCT/US2018/014393, filed Jan. 19, 2018, which claims priority to and the benefit of U.S. Provisional Patent Application No. 62/448,104, filed Jan. 19, 2017, the contents of which are hereby incorporated by reference in their entirety as if fully set forth herein.

FIELD OF THE INVENTION

The present invention relates to wearable devices, and more specifically to wearable devices for reducing lower back muscle stress, fatigue, injury and pain.

BACKGROUND

Lower back pain is a disabling condition experienced by a high percentage of adults within their lifetimes. It is the leading cause of limited physical activity and the second leading cause of missed work in the U.S. and a significant economic burden. Lower back pain is estimated to cost $130-230 billion per year in the U.S. due to medical expenses and lost worker productivity.

Lower back pain is particularly common among individuals who perform repetitive or heavy lifting, due to elevated loading on the lumbar spine that predisposes them to injury risk. Elevated and even moderate loads, applied repetitively to the lumbar spine can increase the risk of lower back pain, weaken or damage the vertebral bodies, and cause intervertebral disc degeneration and herniation. Prolonged leaning and other static postures are also potential risk factors for lower back pain. Combined compression and bending applied repetitively to cadaveric human lumbar spines often causes intervertebral disc injuries. Similarly, elevated and repetitive loading of tissues such as muscles and ligaments can cause strains and damage.

The loading of lumbar muscles, ligaments, vertebrae and discs occurs repeatedly throughout the day during activities such as leaning, lifting, and even sitting. The majority of loading on the lumbar spine is the result of back muscles. Back muscles produce large forces and act at short moment arms about the intervertebral joints to balance moments from the upper-body and external objects. The lumbar spine experiences a large flexion moment during forward leaning of the trunk due to the weight of the upper-body and any additional external loads. To keep the upper-body from falling forward, the flexion moment must be counter-balanced by an extension moment. The extension moment is provided by posterior lumbar muscles which apply forces roughly parallel to the spine. This compressive force caused by the back extensor muscles is exerted on the spine and can cause damage and pain.

Assistance devices such as wearable robots have been designed for industrial or manual material handling work environments, but have form-factors that render them too bulky and impractical for daily at-home use or use in other business, social or clinical settings. For example, to maximize the moment arm and thus mechanical advantage, some of these assistance devices are designed with components that protrude significantly from the lower back. For a daily user, these design features can be restrictive, inhibiting basic activities such as sitting, lying down, stair ascent/descent, or navigating typical home or work environments. Due to the bulky designs, users are also required to wear these devices conspicuously on top of their clothing.

Commercially-available back belts and braces also have not reduced back pain or injury. Often these belts and braces operate by restricting motion of the spine, and attempt to increase intra-abdominal pressure to reduce forces on the spine.

What is needed is an assistance device that can passively offload lumbar muscles and discs during leaning and lifting without restricting spine motion or increasing intra-abdominal pressure. Further, there is a need for such an assistance device to be lightweight, unobtrusive and simple to put on and take off. Finally, there is a need for an assistance device that provides reduced spinal compression forces.

SUMMARY

The various embodiments are directed to wearable devices for reducing lower back muscle stress, fatigue, injury and pain and methods for operating such devices.

In a first embodiment, a wearable lower back assistance device is provided. The wearable assistance device includes an upper-body interface with a front side and a rear side and a lower-body interface with a front side and a rear side. The wearable assistance device also includes one or more elastic members, where each of the elastic members mechanically couples the upper-body interface to the lower-body interface and extending from the rear side of the upper-body interface to the rear side of the lower-body interface and along a back of a user so as to provide an assistive force parallel to the back of the user. The wearable assistance device also includes a clutch mechanism associated with the elastic members, where the clutch mechanism is configured for selectively adjusting the assistive force provided by the one or more of the elastic members.

In some implementations, the wearable assistance device can also include a processor for controlling an operation of the clutch mechanism. Further, the wearable assistance device can also include at least one electromyography sensor communicatively coupled to the processor, and where the processor controls the operation of the clutch mechanism based on an output signal from the at least one electromyography sensor.

In some implementations, the processor is further configured for receiving body dynamics data and adjusting the operation of the clutch mechanism based on the body dynamics data. Alternative, the processor is can be configured for receiving a manual input signal and adjusting the operation of the clutch mechanism based on the manual input signal.

In some implementations, the upper-body interface can be a vest made from a multi-layered sleeve material configured to adhere to a surface of the skin in contact with the sleeve material and to distribute forces over the surface of the skin. Further, the lower-body interface can be a pair of shorts made from a sleeve material configured to adhere to a surface of the skin in contact with the sleeve material and to distribute forces over the surface of the skin.

In some implementations, each of the elastic members can include a first elastic portion and a second elastic portion connected in series, where the first elastic portion is connected to the upper-body interface and where the second elastic portion is connected to the lower-body interface, each of the first elastic portion and the second elastic portion having a different stiffness. In certain implementations, the stiffness of the second elastic portion is greater that the stiffness of the first elastic portion.

In some implementations, the clutch mechanism is mechanically connected to the upper-body interface and is configured to selectively adjust the assistive force provided by the one of the elastic members by selectively engaging and disengaging with the one of the elastic members at a point between the first elastic portion and the second elastic portion.

In some implementations, the one or more elastic members include a first elastic member extending from a right side of the upper-body interface to a left side of the lower-body interface and a second elastic member extending from a left side of the upper-body interface to a right side of the lower-body interface.

In some implementations, further comprising one or more additional elastic members, each of the additional elastic members mechanically coupling the upper-body interface to the lower-body interface, each of the elastic members configured to provide an assistive force parallel to a muscle group other than the back of the user.

In a second embodiment, there is provided a method for operation the wearable assistance device of the first embodiment. The method can include determining, via the processor, whether a current activity of the user requires assistive force. The method can also include, upon determining that the current activity requires assistive force, generating, via the processor, control signals for the clutch mechanism that cause the clutch mechanism to increase the assistive force provided via an associated one of the elastic elements.

In some implementations, the method can also include, upon determining that the current activity requires no assistive force, generating, via the processor, control signals for the powered clutch mechanism, the control signals configured to decrease the assistive force provided via an associated one of the elastic elements.

In some implementations, the determining includes receiving electromyogram (EMG) signals associated with the user, identifying a trend in the EMG signals, and ascertaining whether the current activity requires assistive force based on the trend. In such implementations, the current activity is ascertained to require assistive force is the trend in the EMG signals is increasing. Conversely, the current activity is ascertained to not require assistive force is the trend in the EMG signals is decreasing.

In some implementations, the determining includes receiving, via the processor, body dynamics data for the user and ascertaining whether the current activity requires assistive force based on the body dynamics data. Such body dynamics data can include measurements from EMG sensors, pressure sensors, or force sensors on the user's body.

Figure 12:
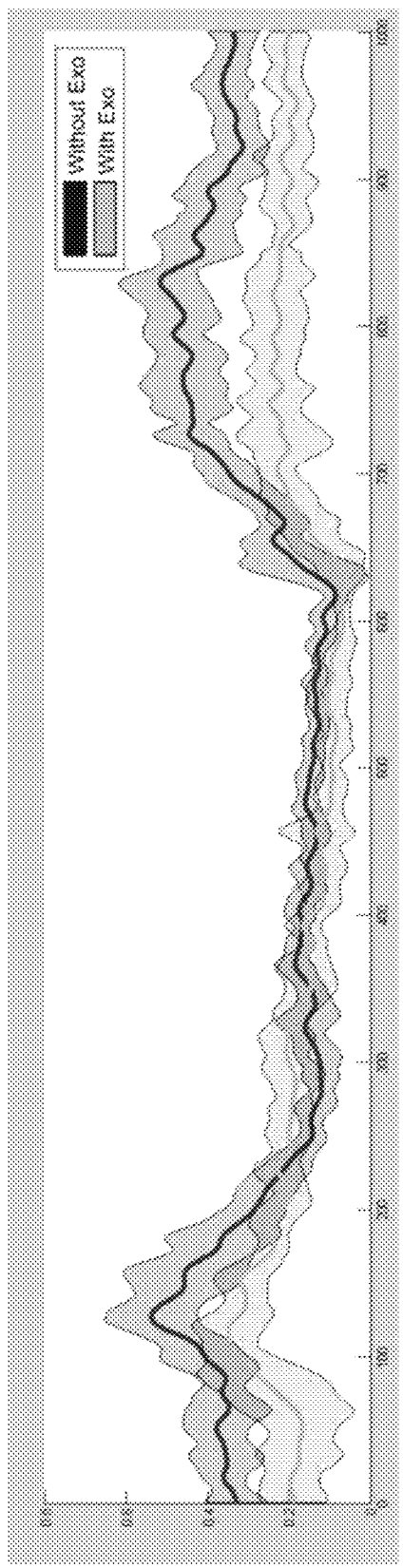

FIG. 12 shows the average erector spinae EMG activity for an individual during lifting of a 28 lb weight versus time (normalized to 1000 data points to represent lifting cycle). The results show reduced EMG activity of the low back muscles while using a wearable assistance device ("with exo") according to an embodiment of the invention as compared to not using any assistance device ("without exo").

Figure 13:
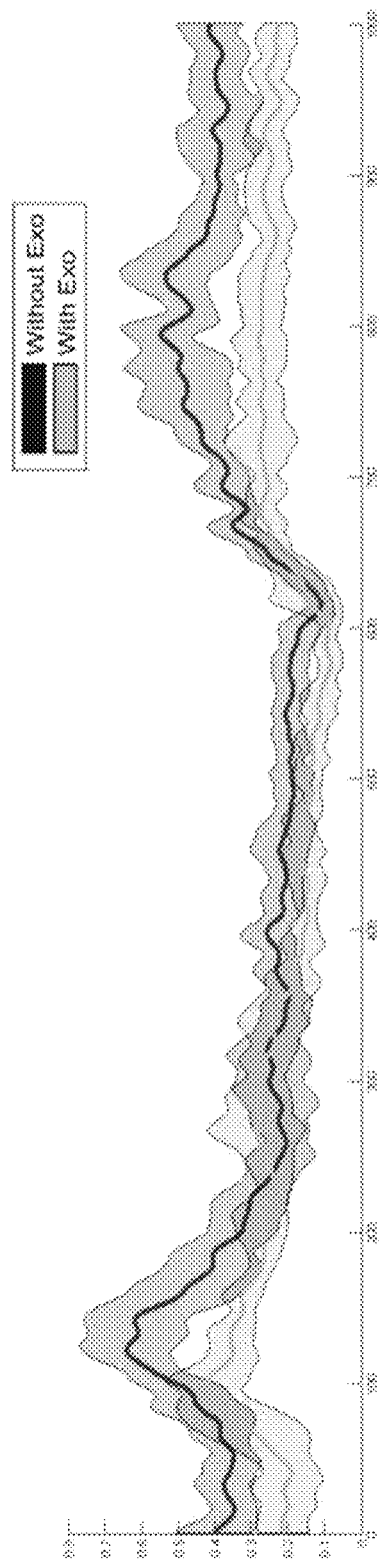

FIG. 13 shows the average erector spinae EMG activity for an individual during lifting of a 53 lb weight versus time (normalized to 1000 data points to represent lifting cycle). The results show reduced EMG activity of the low back muscles while using a wearable assistance device ("with exo") according to an embodiment of the invention as compared to not using any assistance device ("without exo").

Figure 14A:
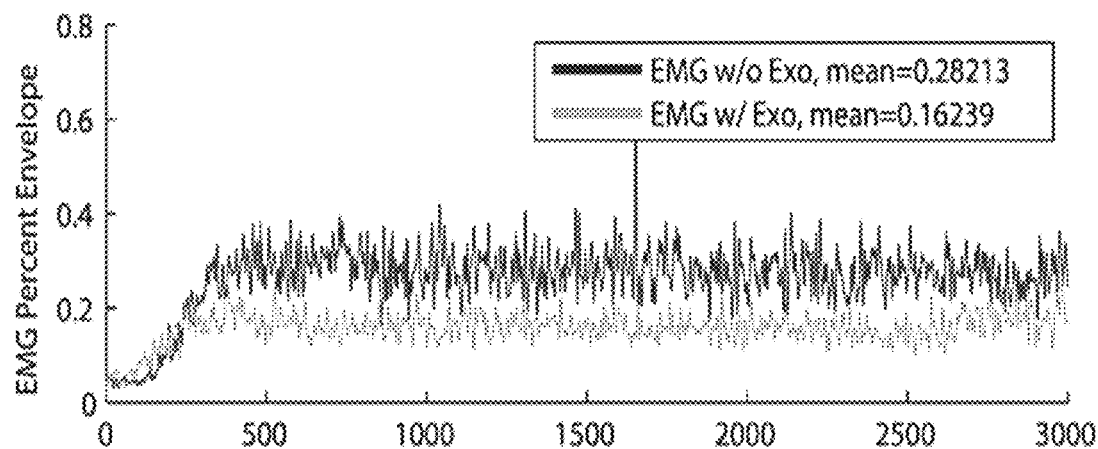

FIG. 14A shows an X-Y plot of EMG activity for a first subject when leaning at a forward angle of 45-60 degrees when wearing a wearable assistance device according to an embodiment of the invention as compared to when not using any assistance device.

Figure 14B:
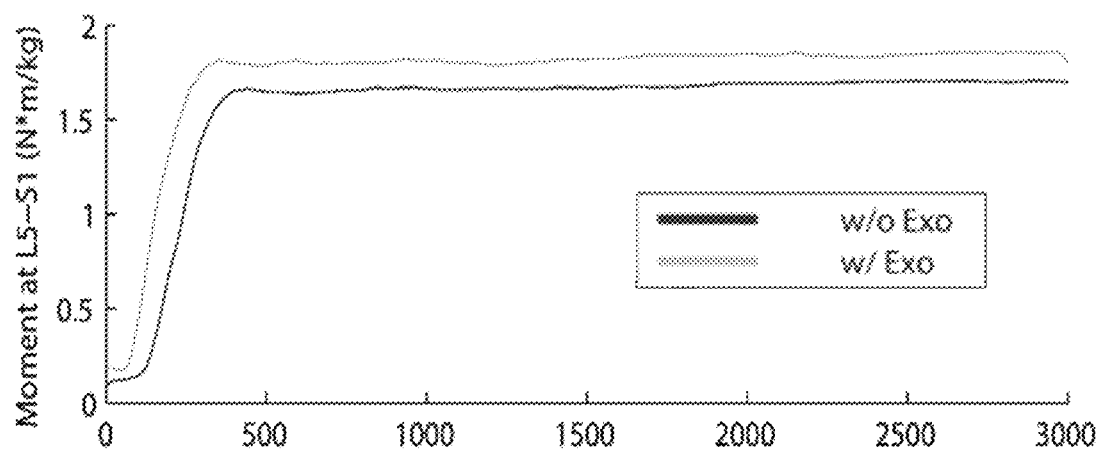

FIG. 14B shows the moment of a first subject's spine when leaning at a forward angle of 45-60 degrees when wearing a wearable assistance device according to an embodiment of the invention as compared to when not using any assistance device.

Figure 15A:
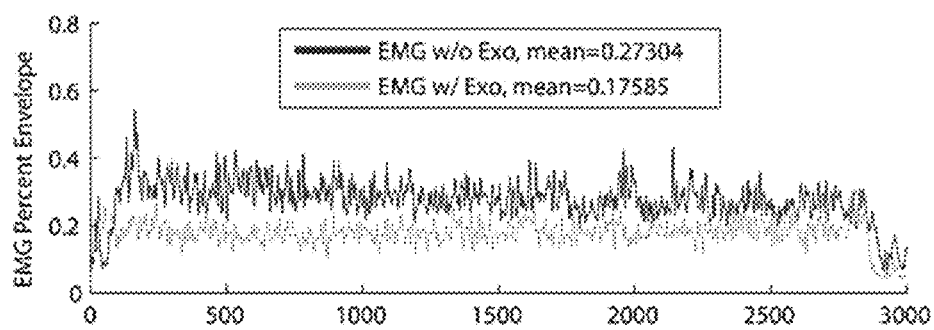

FIG. 15A shows an X-Y plot of EMG activity for a second subject when leaning at a forward angle of 45-60 degrees when wearing a wearable assistance device according to an embodiment of the invention as compared to when not using any assistance device.

Figure 15B:
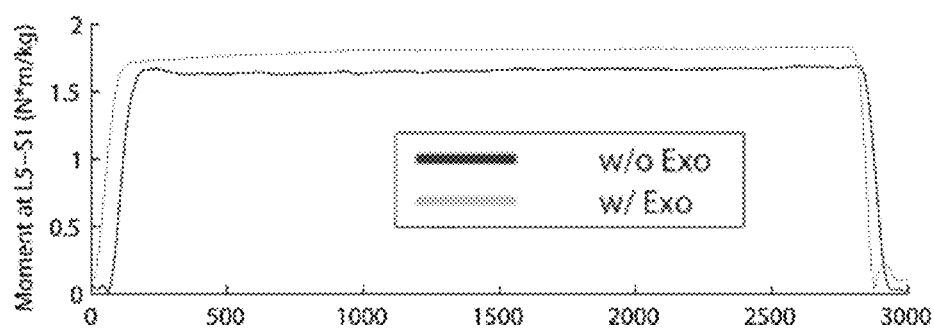

FIG. 15B shows the moment of a second subject's spine when leaning at a forward angle of 45-60 degrees when wearing a wearable assistance device according to an embodiment of the invention as compared to when not using any assistance device.

Figure 16A:
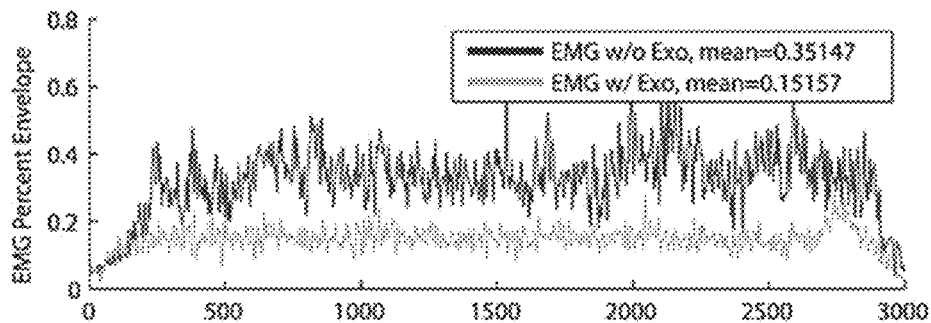

FIG. 16A shows an X-Y plot of EMG activity for a first subject when leaning at a forward angle of 90 degrees when wearing a wearable assistance device according to an embodiment of the invention as compared to when not using any assistance device.

Figure 16B:
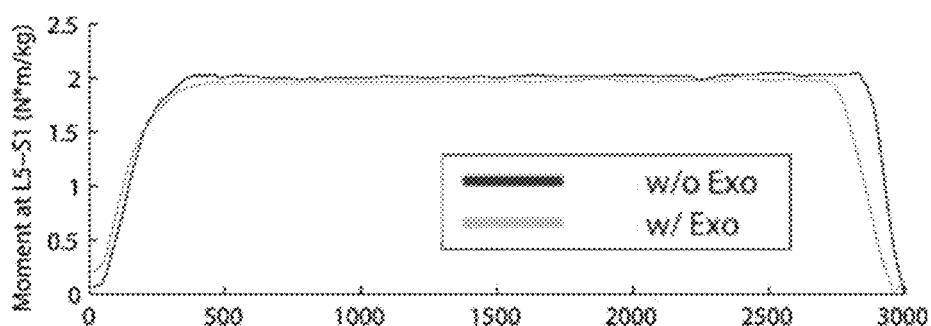

FIG. 16B shows the moment of a first subject's spine when leaning at a forward angle of 90 degrees when wearing a wearable assistance device according to an embodiment of the invention as compared to when not using any assistance device.

Figure 17A:
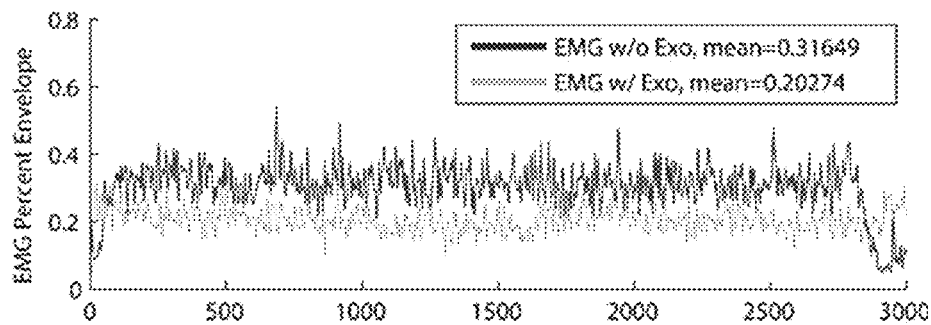

FIG. 17A shows an X-Y plot of EMG activity for a second subject when leaning at a forward angle of 90 degrees when wearing a wearable assistance device according to an embodiment of the invention as compared to when not using any assistance device.

Figure 17B:
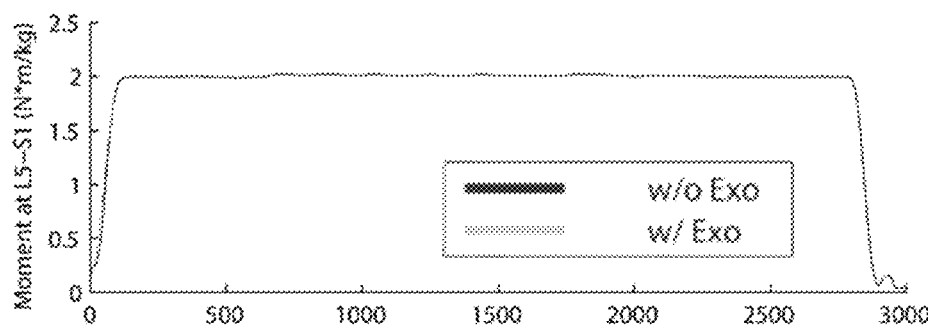

FIG. 17B shows the moment of a second subject's spine when leaning at a forward angle of 90 degrees when wearing a wearable assistance device according to an embodiment of the invention as compared to when not using any assistance device.

Figure 18:
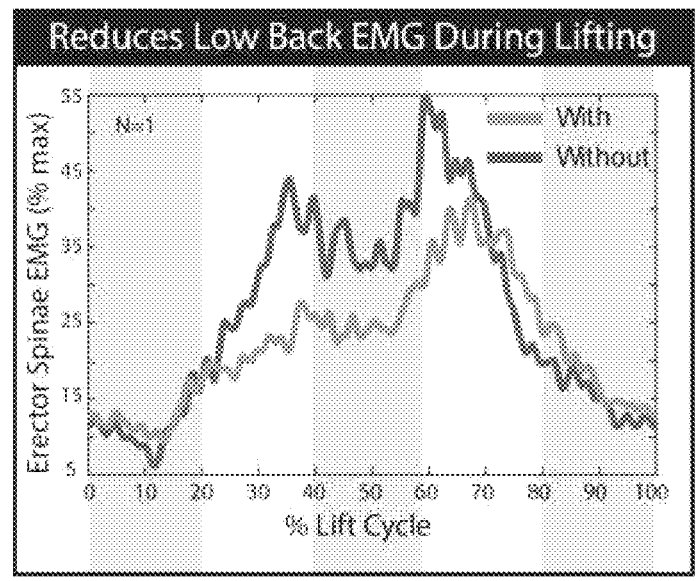

FIG. 18 shows an X-Y plot of erector spinae EMG when wearing a wearable assistance device according to an embodiment of the invention as compared to when not using any assistance device.

Figure 19:
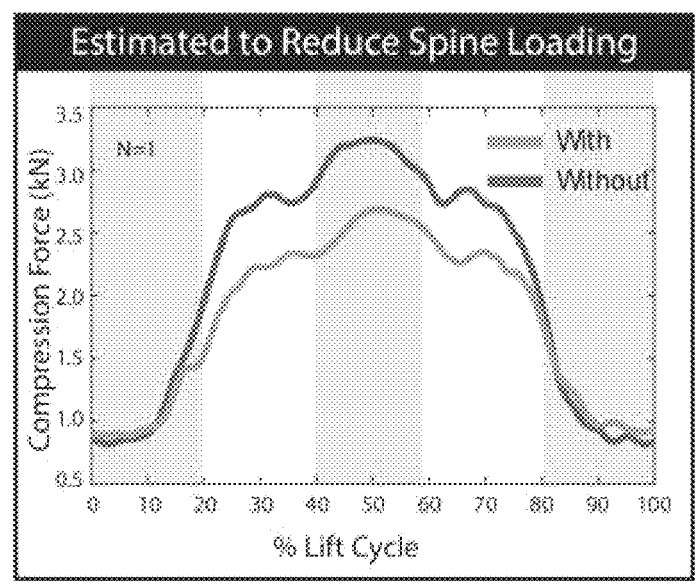

FIG. 19 shows an X-Y plot of the estimated compression force on a user's spine when wearing a wearable assistance device according to an embodiment of the invention as compared to when not using any assistance device.

Figure 20A:
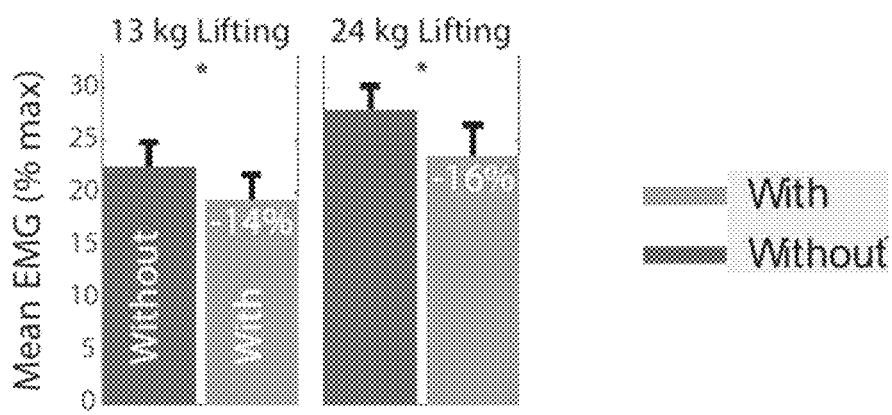

FIG. 20A shows the difference in average EMG activity when lifting different size weights when wearing a wearable assistance device according to an embodiment of the invention as compared to when not using any assistance device (N=8).

Figure 20B:
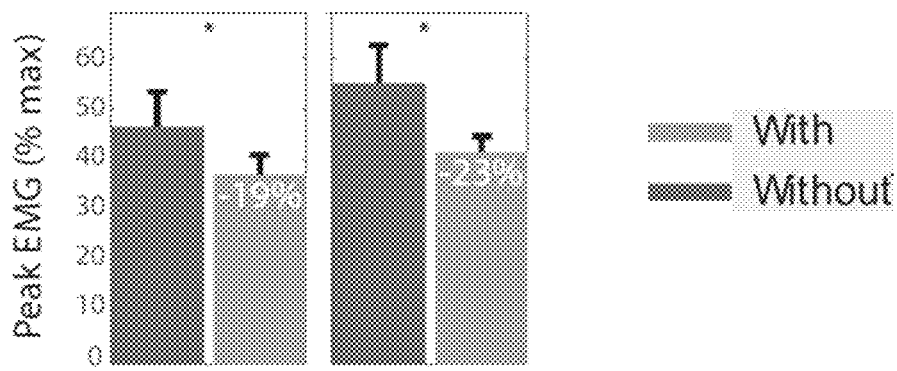

FIG. 20B shows the difference in peak EMG activity when lifting different size weights when wearing a wearable assistance device according to an embodiment of the invention as compared to when not using any assistance device (N=8).

Figure 20C:
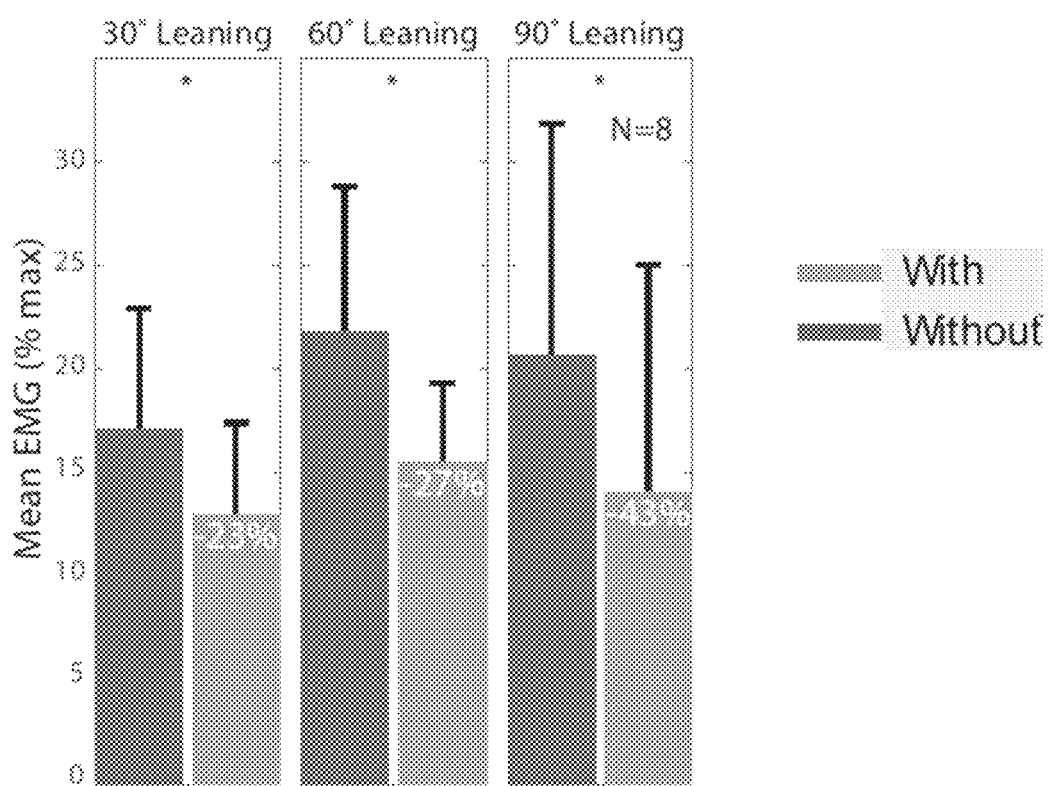

FIG. 20C shows the difference in average EMG activity when leaning at different angles when wearing a wearable assistance device according to an embodiment of the invention as compared to when not using any assistance device (N=8).

Figure 21:
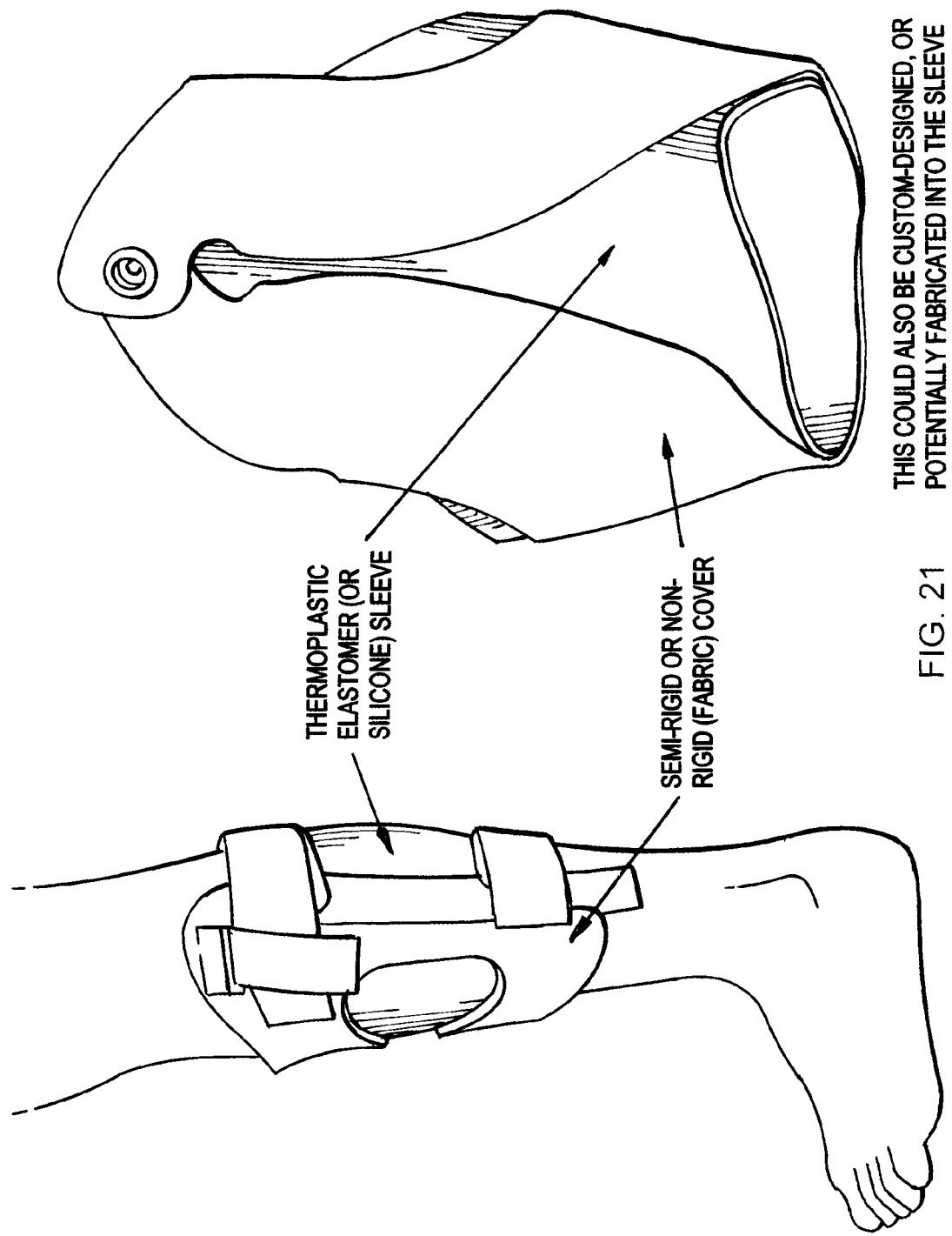

FIG. 21 shows an illustration of a multi-layered sleeve and cover used for an upper and lower-body interface according to an embodiment of the invention.

Figure 22:
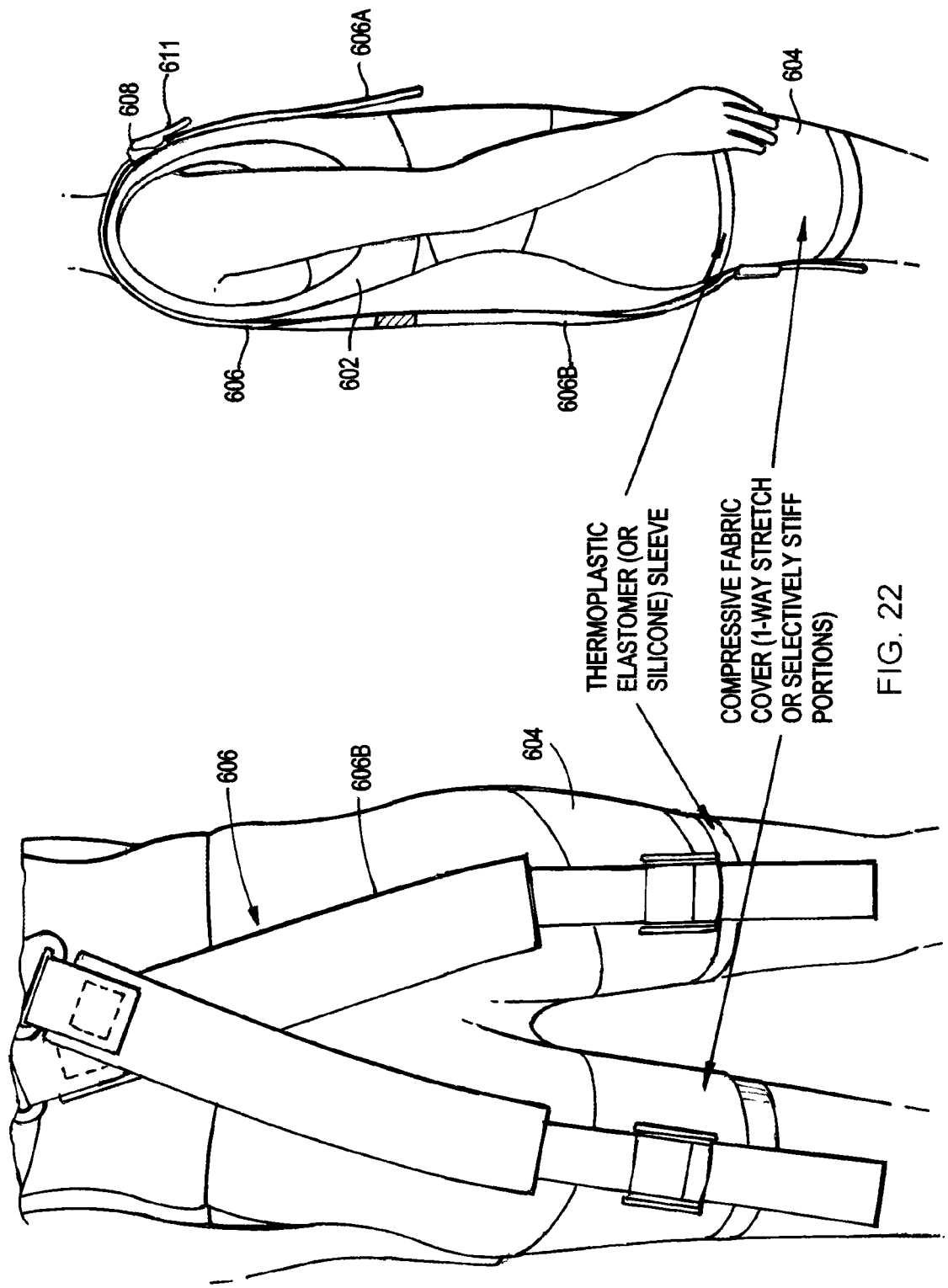

FIG. 22 is a side perspective view and a rear perspective view illustration of the material used for a lower-body interface according to the various embodiments.

FIG. 23 shows the material of FIG. 22 implemented in a lower-body interface according to the various embodiments.

Figure 24:
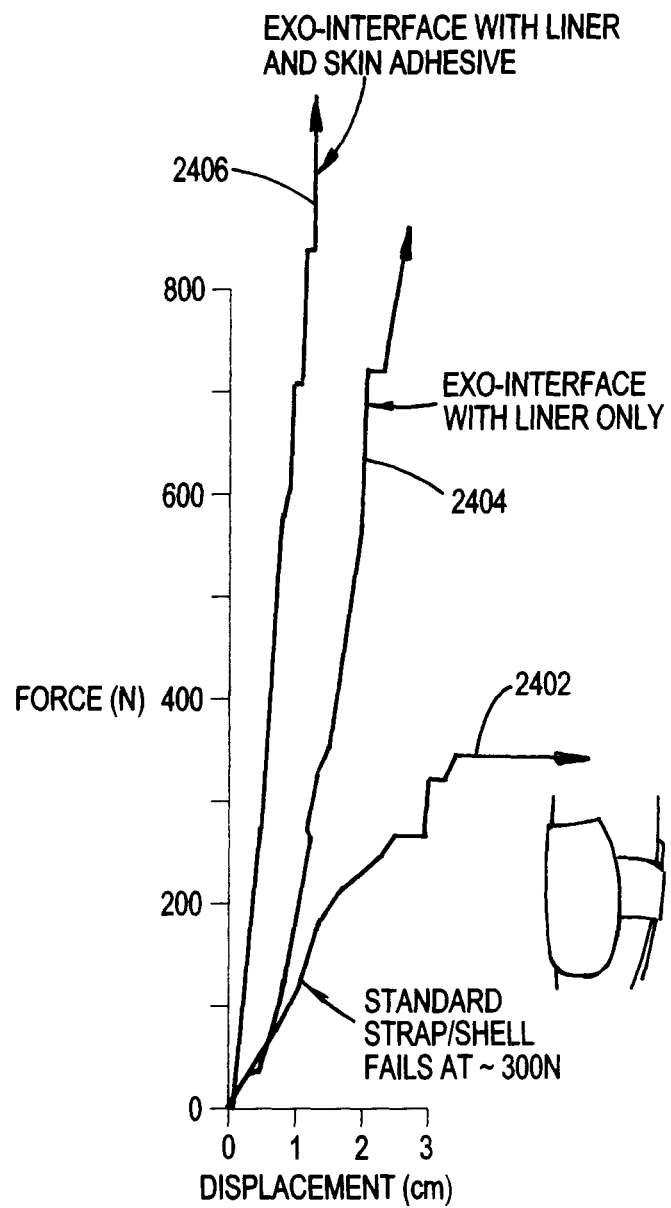

FIG. 24 shows an X-Y plot of the force and displacement during mechanical testing of different materials for various embodiments.

Figure 25:
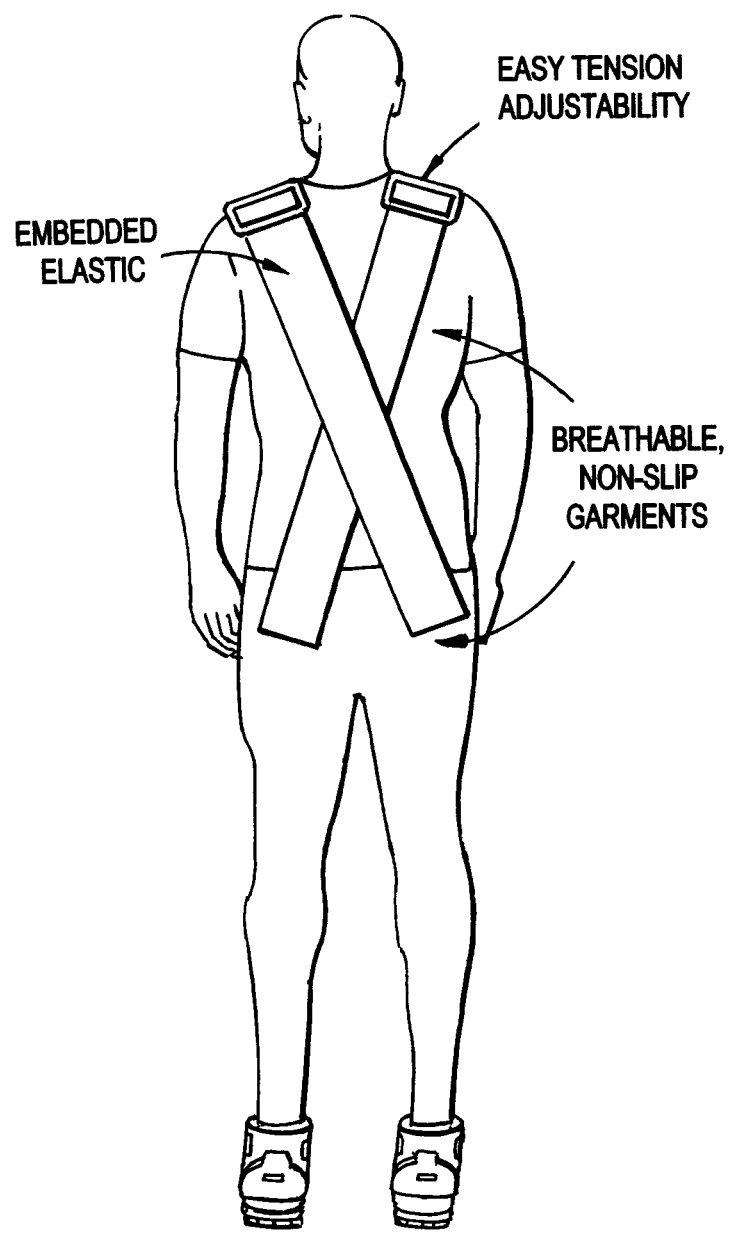

FIG. 25 shows rear perspective views illustrating an clothing integrating a wearable device according to an embodiment. In this instance the clutch may be located on the top or front of the shoulder, to allow for easy adjustability of assistance.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments are directed to wearable assistance devices, such as an exoskeleton or a garment, that can assist a wearer with leaning and lifting tasks. In particular, such assistance devices can provide a separate lumbar extension moment from the wearer's lower back when the wearer leans forward. Elastic bands in an exemplary embodiment provide equivalent extensor moments to the wearer's muscles with smaller force magnitudes. However, any other type of elastic member(s), viscoelastic member(s), or spring-type devices can be used in place of the elastic bands, as discussed in greater detail below. This results in reduced forces on the low back muscles, which then reduces lumbar disc loading. In this way, these wearable assistance devices can help mitigate overuse and overloading of the erector spinae muscles (and other back muscles and ligaments) that commonly leads to lower back injury and pain. In particular, the wearable assistance devices of the various embodiments are configured to transmit loads directly to the legs which allows forces to bypass the lower back muscles and the intervertebral discs.

Wearable assistance devices in accordance with the various embodiments can assist with lifting, carrying or leaning tasks, transitioning from sit to stand or stand to sit, and other forms of locomotion. Further, the wearable assistance devices can be configured to span additional joints beyond the lower back such as the knee or neck to provide assistance for specific tasks.

Wearable assistance devices according to the various embodiments can provide weak or strong assistance, corresponding to a lower degree of support or a higher degree of support, respectively, during a task. In particular, the transition from weak to strong assistance, or vice versa, can be triggered by engaging a clutch mechanism that adjusts the strength of any devices that provide equivalent extensor moments to the wearer's muscles. The amount of assistance (assistive force) can be selected manually or can be triggered from signals receives from one or more wearable sensors. Such sensors can be separate or integrated into the wearable assistance device.

Figure 1:
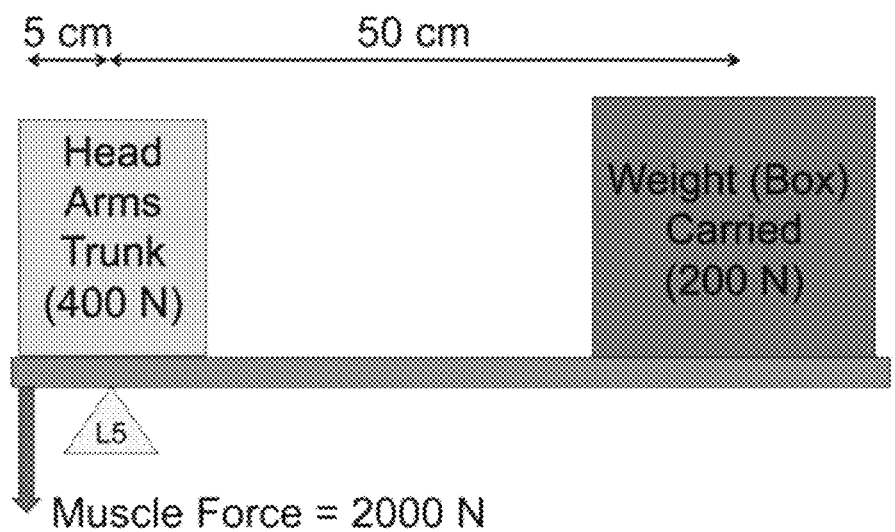
FIG. 1 shows the various forces on the back when lifting an object.

FIG. 1 shows a simplified biomechanical model of lifting a box. The diagram is useful for demonstrating why high spinal forces arise from muscles acting at short moment arms. In FIG. 1, lifting and carrying a box can be modeled as a simple lever system where the fulcrum is located at the lumbar vertebrae and disc. FIG. 1 shows how the mass of a person's trunk and the mass of a carried weight applies a collective force to the spine. In this example, the trunk of a person contributes 400 Newtons (N) while the weight of the box contributes 200 N. To prevent the trunk from pitching forward due to the carried load, the lower back musculature must create a counter-acting moment to the forces. In the example of FIG. 1, the muscle force required to provide this moment is 2000 N, which can be calculated based on the depicted moment arms. The total spine force is then the sum of the required muscle force, the force from the weight of the box, and the force from the weight of the person's trunk. Thus, the total spine force is 2600 N, of which 75% is due to the muscle force.

Spine ligaments have shorter moment arms than their corresponding muscles, which means that loading those tissues results in higher spinal forces. Additionally, co-contraction of the abdominal muscles when moving also increases spine loads. Altogether, FIG. 1 demonstrates how a simple lifting of a box can result in an excessive load on a person's spine.

Figure 2:
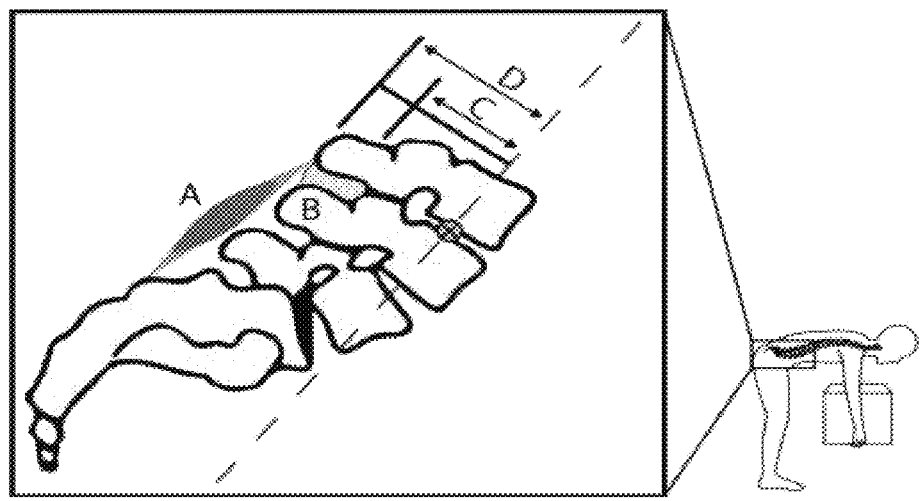
FIG. 2 shows low back extensors muscles and ligaments, which provide moment around the spine during forward leaning.

FIG. 2 illustrates the compression which occurs in the lumbar spine as a result of muscle and passive tissue forces during forward leaning. The region labeled A shows muscle attached to the lumbar spine which causes compression during leaning. The region labeled B refers to the tissue in between vertebrae spine which passively causes compression. The region labeled C shows how ligaments and other passive tissues act across a small moment.

The majority of loading on the lumbar spine is the result of back muscles which produce large forces and act at short moment arms about the intervertebral joints in order to balance moments from the upper-body (such as when leaning) and any external objects (such as when lifting). Consequently, the lumbar spine experiences a large flexion moment during forward leaning of the trunk due to the weight of the upper-body and any external loads. To keep the upper-body from falling forward, the flexion moment (D in FIG. 2) must be counter-balanced by an extension moment (C in FIG. 2). The extension moment is provided by posterior lumbar muscles (A) and passive tissues (B). However, passive tissues act at a small extensor moment arm of approximately 3-7 centimeters (cm) relative to the center of the vertebral bodies. Therefore, these tissues have to experience large forces to generate the required counter-balancing moment. Active and passive tissues apply forces roughly parallel to the spine. When loaded, the tissues apply substantial compressive forces to the spine. The compressive force caused by the back extensor muscles constitutes the majority of the compressive force experienced by the spine during forward leaning.

Figure 3:
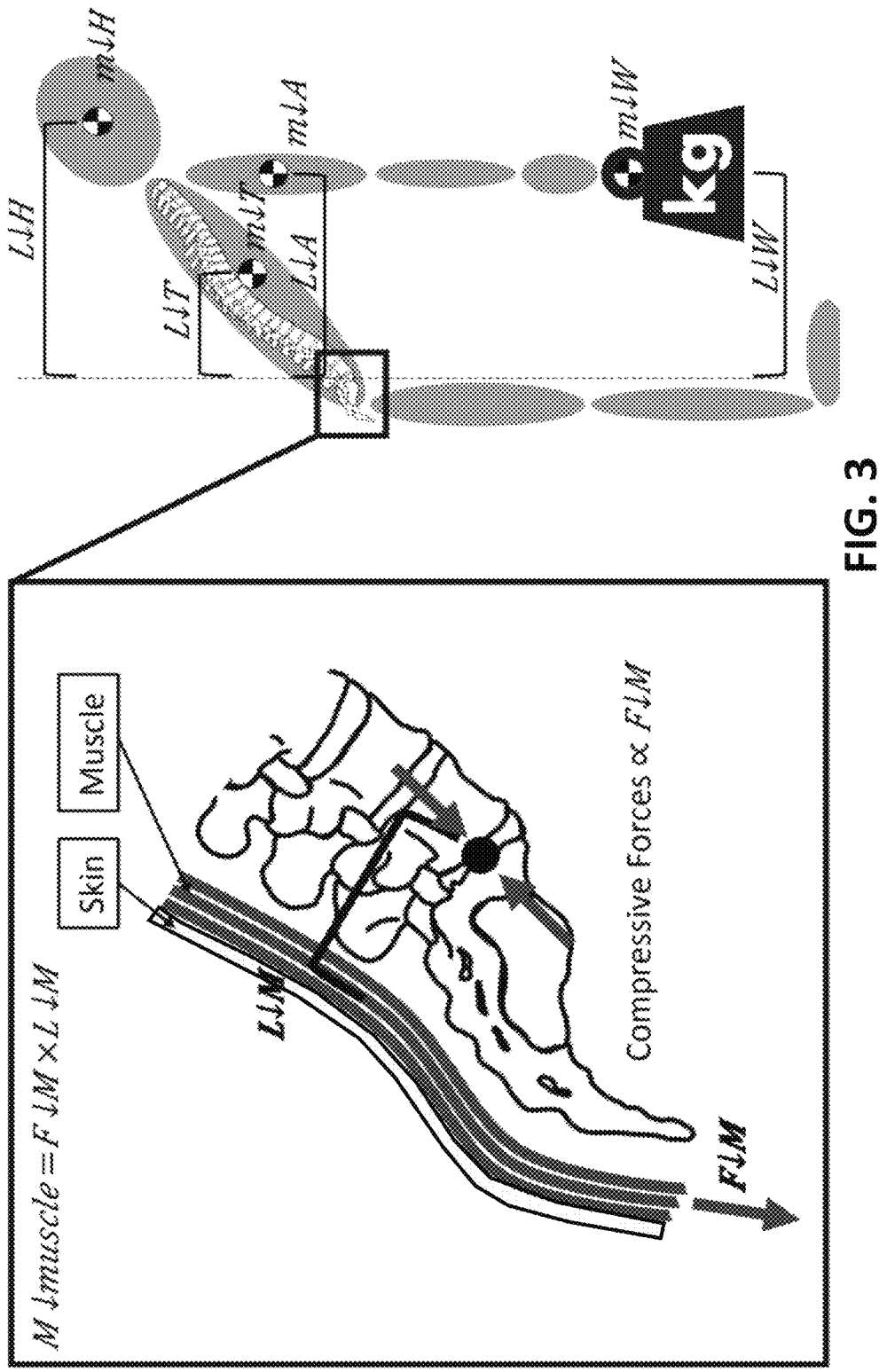
FIG. 3 illustrates the masses that cause flexion moment about the spine during leaning and lifting, and also the low back muscles that counteract this moment.

FIG. 3 is an anatomical diagram further showing in detail the forces on the lumbar spine during leaning or lifting. The muscle (3 layers shown in FIG. 3) sits underneath the skin and against the lumbar spine. Muscle force pulls downward on the spine. Compressive force presses upwards against the moment. The weight pulls downward against the spine and is seen held by the person in the diagram. However, the force of the weight being lifted is but one source of the compressive force on the spine. Up to four additional sources of compressive force on the spine can be identified.

A first source is the person's head when leaning over. In FIG. 3, this is shown by $L{\downarrow}H$ and $m{\downarrow}H$, where $L{\downarrow}H$ refers to the distance from the lumbar spine to the center of mass of the person's head and $m{\downarrow}H$ refers to the weight of the person's head. A second source is the person's trunk. In FIG. 3, this is shown by $L{\downarrow}T$ and $m{\downarrow}T$, where $L{\downarrow}T$ refers to the distance from the lumbar spine moment to the center of mass of a person's trunk and $m{\downarrow}T$ refers to the weight of a person's trunk. A third source is the person's arms. In FIG. 3, this is shown by $L{\downarrow}A$ and $m{\downarrow}A$, where $L{\downarrow}A$ refers to the distance from the lumbar spine moment to the center of mass of a person's arms and $m{\downarrow}A$ refers to the weight of a person's arms. The final source is the weight being carried. In FIG. 3, this is shown by $L{\downarrow}W$ and $m{\downarrow}W$, where $L{\downarrow}W$ refers to the distance between the lumbar spine moment and the center of mass of a carried load and $m{\downarrow}W$ refers to the weight of a carried load.

As discussed above, a person's lower back muscle must provide a counter-balancing moment to the moment of a carried load. The distance between the lower back muscle and the lumbar spine moment is represented by $L{\downarrow}M$. The counterbalancing muscle moment must equal the cross product of compressive forces ($F{\downarrow}M$) and the distance from the lumbar spine moment to the center of mass for the person and the carried load ($L{\downarrow}M$). Thus, as $L{\downarrow}M$ would be exceedingly small compared to the distances $L{\downarrow}H$, $L{\downarrow}T$, $L{\downarrow}A$, and $L{\downarrow}W$, the amount of counterbalancing muscle force is significant, and amount of compression on the spine is significant as well.

In view of the foregoing, a wearable assistance device in accordance with the various embodiments is configured to allow a user to selectively reduce the necessary counterbalancing muscle forces. Consequently, the amount of spinal compression is expected to be reduced as well. This is illustrated below with respect to FIGS. 4A and 4B.

Figure 4A:
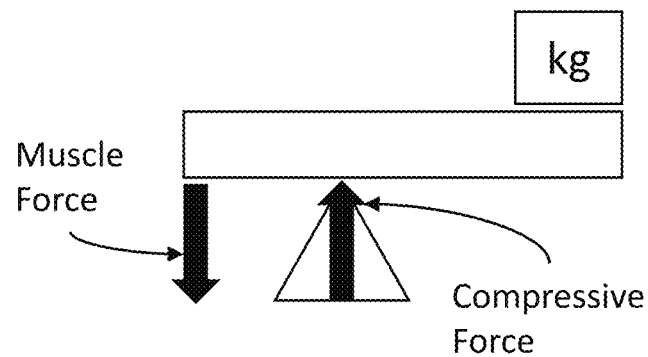
FIG. 4A shows the compressive force on the spine when lifting a weight.
Figure 4B:
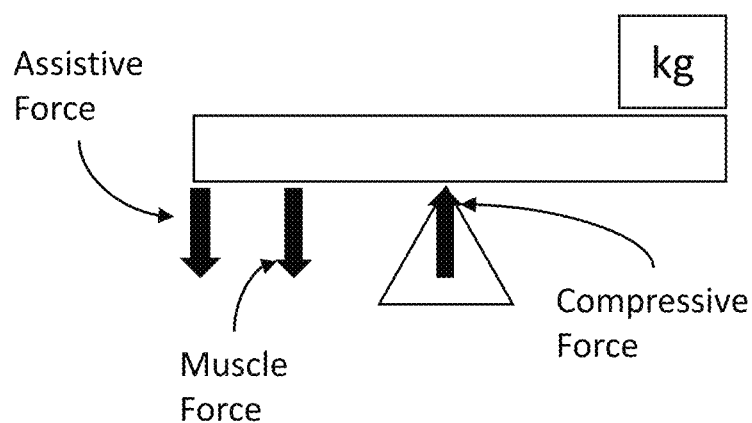
FIG. 4B shows the compressive force on the spine when wearing an assistance device according to an embodiment of the present disclosure.

FIGS. 4A and 4B show, respectively, diagrams of the compressive force pushing against a lumbar spine without muscle force assistance for the lower back and with muscle force assistance for the lower back. FIG. 4A shows that without any assistance, the muscle force exerts all its force on a moment very close to the lumbar spine, similar to the scenario discussed above with respect to FIG. 1. Thus, a high compressive force on the spine is generated to counterbalance the muscle forces. However, when muscle force assistance is provided for the lower back in parallel with the normal muscle forces, a more favorable result is obtained. This is illustrated in FIG. 4B. That is, by providing a wearable device that provides distance between the lumbar spine and the force pushing down, less force needs to be generated by the muscle for the lifting task, in order to achieve an equivalent moment about the spine. Consequently, a lower compressive force on the spine is generated due to these lower muscle forces.

Figure 5:
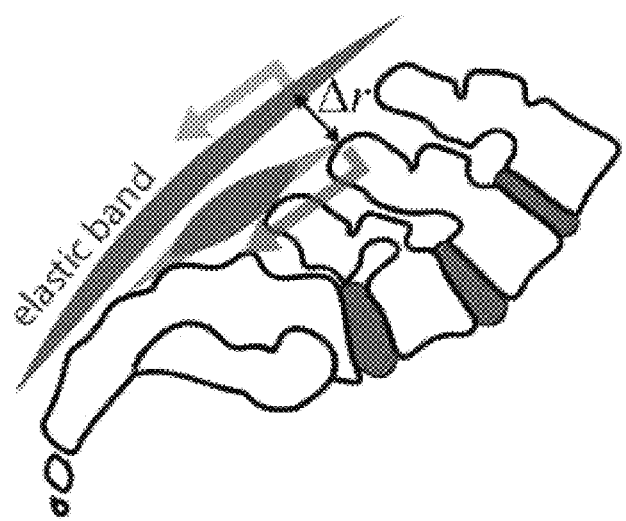
FIG. 5 illustrates the force borne by an elastic band has a larger moment arm about the spine, relative to the force of a user's muscle.

FIG. 5 shows how applying an external assistive force parallel with lower back musculature and connective tissue can provide an assistive extensor moment. Such an external assistive force reduces spinal disc and muscle forces by effectively increasing the extensor moment arm about the vertebrae/discs. Namely, the assistive force is provided outside the body. The assistive force provides a larger extensor moment arm compared to that for the muscle forces. The assistive force effectively provides an equivalent moment with a smaller force which reduces the resultant spinal compression force. In FIG. 5, Ar represents the added distance to the moment arm from an elastic band or similar mechanical element, according to an embodiment of the present disclosure. The elastic band shown in FIG. 5 stretches during leaning and lifting activity of the wearer to offload lumbar extensors. However, the restorative force of the elastic band supplies an assistive force with the larger extensor moment.

The various embodiments leverage the foregoing concepts to provide a wearable assistance device that reduces spinal disc and muscle forces by effectively increasing the extensor moment arm about the vertebrae/discs. Moreover, the various embodiments allow the person using the wearable assistance device to selectively adjust the amount of assistance (i.e., the amount of assistive force) needed by engaging and disengaging at least one elastic member. In this way, during a lifting or leaning task, the device can be adjusted to provide strong assistance but remain comfortable for non-lifting or non-leaning tasks. In particular, by providing weak or no assistance, the device is flexible and allows freer motion by the user for everyday tasks. An exemplary configuration of such a wearable assistance device is shown in FIG. 6A-6C.

Figure 6A:
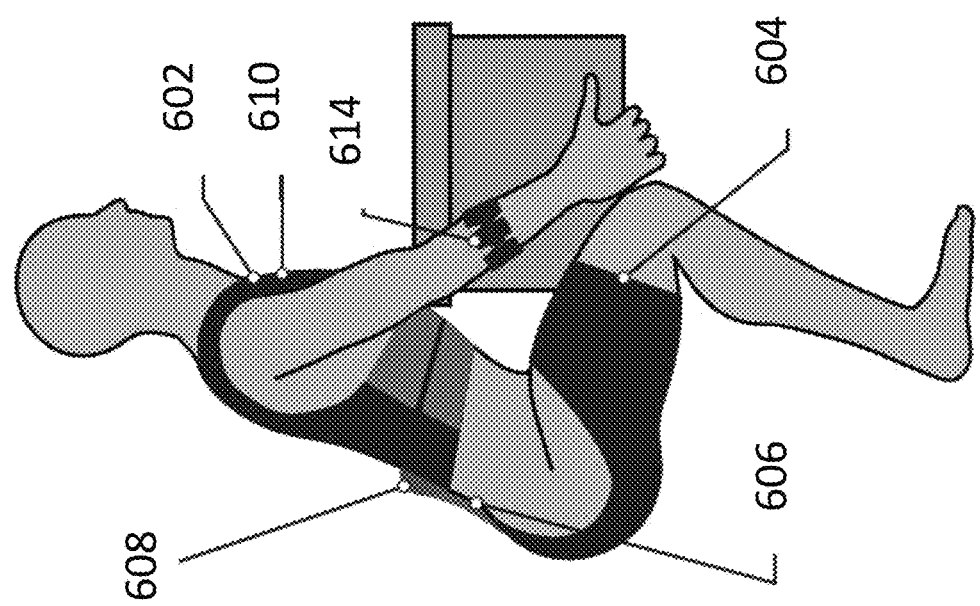
FIG. 6A is a side perspective view illustration of an exemplary wearable assistance device according to the present disclosure.
Figure 6C:
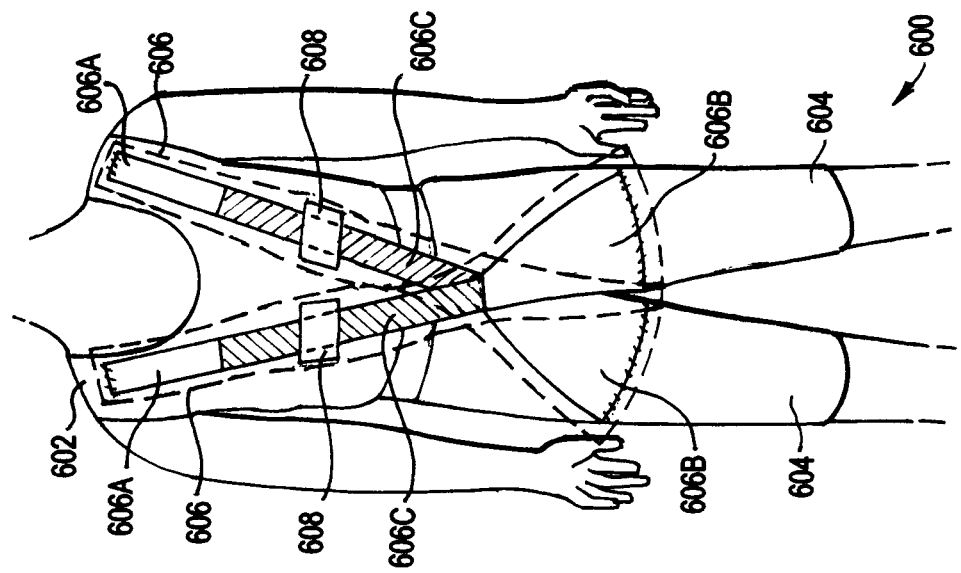
FIG. 6C is a back view of a wearable assistance device according to an embodiment of the invention.
Figure 6B:
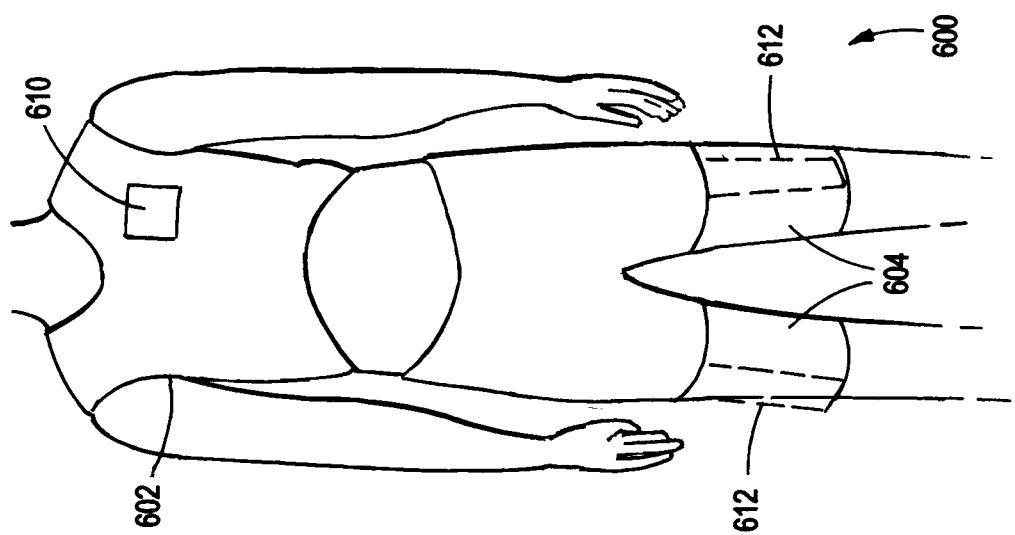
FIG. 6B is a front view of a wearable assistance device according to an embodiment of the invention.

FIG. 6A-6C shows an exemplary wearable assistance device 600 in accordance with the various embodiments. FIG. 6A shows a side view of the wearable assistance device 600. FIG. 6B shows a front view of the wearable assistance device 600. FIG. 6C shows a rear view of the wearable assistance device. The wearable assistance device 600 includes an upper-body interface 602, a lower-body interface 604, one or more elastic member 606, and a clutch 608. The wearable assistance device 600 can optionally include a processor 610. Each of these components will be discussed in greater detail below.

The upper-body interface 602 can be a garment configured as a vest which can be put on and taken off by a user. For example, the interface can be put on and taken off through the use of a zipper, buttons, snaps, straps, or any other type of fasteners for garments. In the configuration illustrated in FIGS. 6A-6C, the upper-body interface is configured as a vest that contains holes for the wearer's arms and head while extending roughly halfway down on the wearer's torso. The vest is configured to bear the weight of a load carried by the wearer and to distribute force over the wearer's shoulders, back, and chest. Additional loading is directed through the elastic members 606 down to the lower-body interface 604.

The lower-body interface 604 can also be a garment that can be put on and off by the user. In the configuration of FIGS. 6A-6C, the lower-body interface 604 is configured as a pair of shorts which can be pulled on and off by the user. The pair of shorts cover the majority of the wearer's thighs and distribute pressure over the surface area of the shorts. In some embodiments, the shorts can be made of an elastic material that adapts and conforms to the wearer's thighs, thus ensuring a good fit. In some implementations, straps, lacing, or other securing elements can be provided in the shorts to ensure that the shorts do not run up the user's thighs when the wearable assistance device 600 is in use. For example, as shown in FIG. 6B, the lower body interface includes a securing mechanism 612 for each thigh.

Figure 6D:
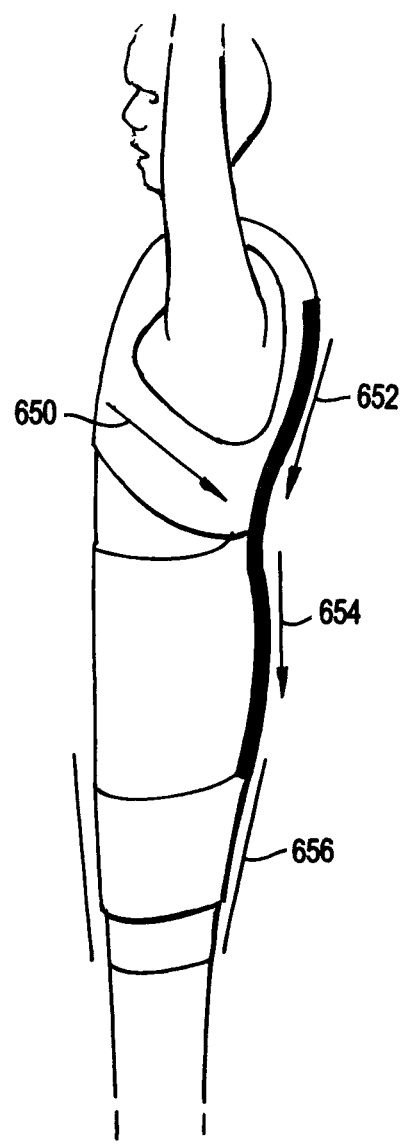
FIG. 6D is a side view of a wearable assistance device according to an embodiment of the invention.
Figure 10A:
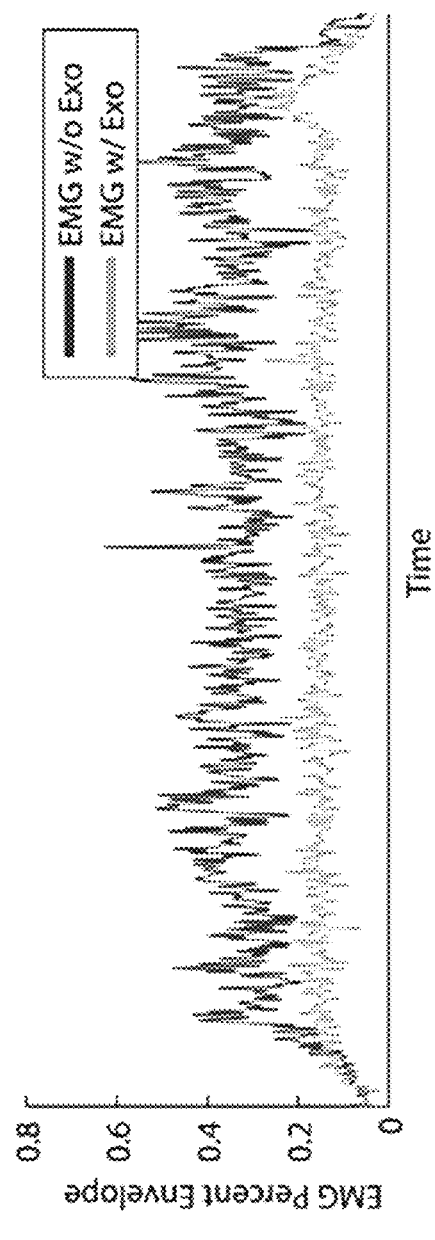
FIG. 10A is an X-Y plot of a user's EMG activity when wearing a wearable assistance device according to an embodiment of the invention as compared to when not using any wearable assistance device.

FIG. 6D shows how the applied forces are distributed through the upper-body 602 and lower-body 604 interfaces when a user dons the wearable assistance device 600. As shown by arrow 650 and 652 in FIG. 6D, the upper-body interface is configured to distribute forces not only along the back of the user, but also along the sides of torso of the user. Thus, forces are not distributed solely along the user's back when performing tasks. These forces are then transferred to the lower-body interface, as shown by arrow 654. FIG. 10A also shows how the thigh interfaces are designed with a taper 656 which prevents the interfaces from sliding up the thigh during use. This taper conforms to the typical, conical shape of the thigh.

As noted above, the upper-body interface 602 and the lower-body interface 604 are connected via one or more elastic member 606 to allow forces to be transferred from the upper-body interface 602 to the lower-body interface 604. For example, as shown in FIGS. 6A-6C, two elastic members 606 are configured to couple the vest defining the upper-body interface 602 and the shorts defining the lower body interface 604 by extending from the back of the vest to the back of the pair of shorts in parallel with the back of the user.

In the various embodiments, the elastic member 606 shown consists of a first elastic portion 606A connected to a second elastic portion 606B. In some embodiments, the elastic member can also include an intermediate portion 606C connecting portions 606A and 606B, as shown in FIG. 6C. In such embodiments, the intermediate portion can be constructed from materials that can be repeatedly subjected to pressure from the clutch 608. For example, in some embodiments, portions 606A and 606B can be constructed from elastic materials (e.g., rubber, plastics, or the like) and the intermediate portion 606C can be constructed from nylon webbing or fabric or from any other type of durable fabrics or webbings. However, in other embodiments, no intermediate portion can be provided. Alternatively, the elastic member 606 can include additional portions, including elastic and non-elastic portions. For example, additional portions can be provided to connect portions 606A and 606B to upper-body interface 602 and lower-body interface 604, respectively.

As shown FIG. 6A-6C, the exemplary embodiment of wearable assistance device 600 includes a pair of elastic members 606 and respective clutches 608. As shown in FIG. 6C, these are provided in an overlapping arrangement. Such an arrangement lowers the probability that the elastic members will become entangled. However, the various embodiments are not limited to any particular number of arrangement of elastic member and clutches.

In the various embodiments, the first elastic portion 606A is configured to have a low stiffness and the second elastic portion 606B is configured to have a high stiffness. These elastic portions 606A and 606B are connected in series. The elastic member 606 is, in turn, configured to pass through clutch 608 so as to allow clutch 608 to selectively adjust a stiffness of the resulting spring between upper-body interface 602 and lower-body interface 604. Thus, the amount of assistive force provided by the elastic member 606 is also adjusted. This is schematically illustrated with respect to FIG. 7A-7C.

As noted above, one aspect of the various embodiments is the use of a clutch mechanism integrated into the wearable assistance device so that wearer can selectively engage and disengage the elastic assistance. Wearers are typically not performing leaning or lifting tasks 100% of the time, so a clutch allows wearers to 'turn off' the elastic assistance when it is not needed. For example, a wearer typically does not need elastic assistance during walking or sitting down. In such scenarios, the wearer can then 'turn on' the elastic assistance when it is needed without the need to take on or off the entire device.

Figure 7C:
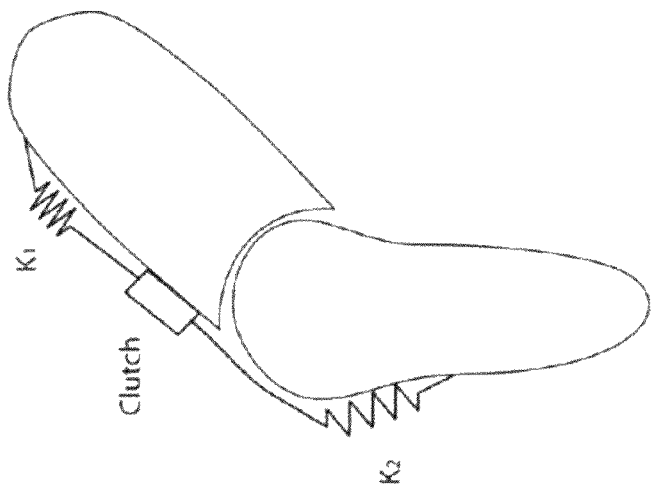
FIG. 7C shows a side perspective view of the load on each spring of a clutch mechanism while the clutch mechanism is engaged.
Figure 7B:
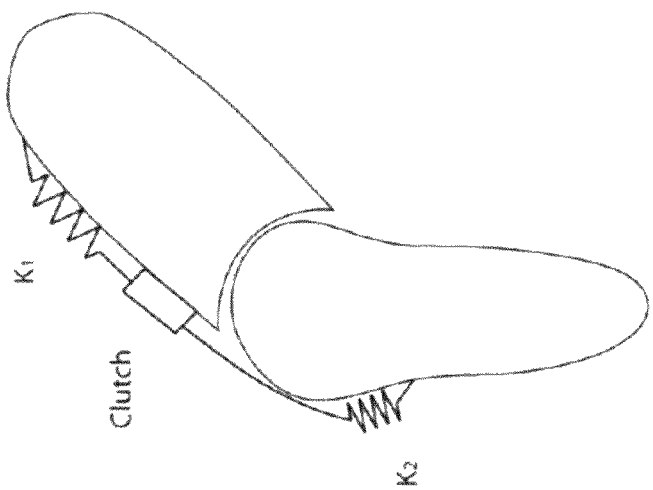
FIG. 7B shows a side perspective view of the load on each spring of a clutch mechanism while the clutch mechanism is not engaged.
Figure 7A:
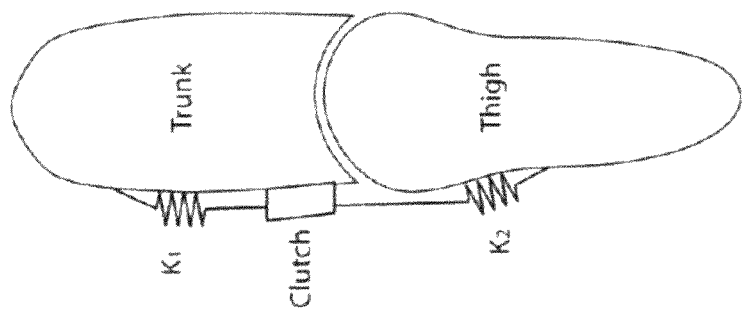
FIG. 7A shows a side perspective view of a clutch mechanism used to attach a lower-body interface and an upper-body interface.

FIGS. 7A-7C shows the configuration and operation of clutch mechanism in accordance with the various embodiments. In the various embodiments, the clutch can be an electromechanical or mechanical mechanism configured to operate with an elastic member, such as elastic member 606 in FIG. 6A-6C, to selectively adjust the amount of assistance to be provided.

FIG. 7A schematically illustrates the arrangement and operation of the clutch mechanism and the elastic member in accordance with an embodiment. As shown in FIG. 7A, an elastic member with two elastic portions (such as that discussed above with respect to FIGS. 6A-6C) can be modeled as a series arrangement of two springs to provide forces in parallel with the lower back during leaning or lifting activities. As discussed above with respect to FIGS. 6A-6C, one spring (labeled K1 in FIG. 7A) can be connected to the person's trunk (via an upper-body interface). A second spring (labeled K2 in FIG. 7A) can be relatively stiffer or stronger that the first spring and can be connected to the person's thigh (via a lower-body interface). For K1 and K2, the assistive force of each of the springs will be essentially the amount of restorative force generated by each of these springs when they are stretched or otherwise deformed. Thus, the higher the stiffness, the higher the restorative force, and therefore the higher the assistive force.

When assistance is not needed, the clutch can be disengaged. In such a configuration, the elastic member that connects the upper-body interface to the lower-body interface (i.e., the series combination of K1 and K2) can slide freely through the clutch housing. Thus, the weaker spring (K1) deforms first in response to leaning or lifting. This is illustrated in FIG. 7B by the stretching of K1. However, since K1 has a lower stiffness and K2 does not deform, the overall restorative force will be relatively low. As a result, little or no assistive force is provided when leaning or lifting with the clutch disengaged. Thus, a disengaged clutch allows a wearer to move, bend, and lean with negligible resistance to their movements.

Although the weak spring K1 stretches as the wearer leans forward and applies minimal resistance to movement, the weak spring K1 can be configured so as to provide enough restorative force to keep the elastic member taut. This can help ensure that the upper-body interface, the lower-body interface, and clutch do not fall or protrude from the wearer's back.

When assistance is needed, the clutch can be engaged such that the load path between the upper-body interface and the lower-body interface goes only through the stiff spring K2 and not through spring K1. In such a configuration, the elastic member that connects the upper-body interface to the lower-body interface (i.e., the series combination of K1 and K2) can no longer slide freely through the clutch housing. Thus, the stiffer spring K2 is fixed at the clutch when the clutch is engaged. This forces the stiff spring K2 to stretch as the wearer leans forward. In this configuration, because the stiff spring K2 acts in parallel with lower back muscles and its higher stiffness results in a higher restorative force, an assistive force is provided and reduces muscle effort during leaning.

In some implementations, the stiffnesses of the K1 and K2 can be reversed. Thus, in order to provide the same functionality as described above, the location of the clutch mechanism can be changed so that when the clutch mechanism is engaged, the stiffer spring, K1, provides assistive force. For example, the clutch mechanism can be located on the lower-body interface instead of the upper body interface.

In still other implementations, the arrangement of the elastic member can be configured so as to provide support when the clutch is disengaged instead of when the clutch is engaged. In such a configuration, the stiffnesses of K1 and K2 are reversed. Thus, when the clutch is engaged, only the lower stiffness spring is used and little assistance is provided. When the clutch is engaged, the combined stiffness is higher, providing some assistance.

In some embodiments, the wearable assistance device can have multiple levels of assistance. For example, the elastic member can be defined using two or more elastic members that are configured in parallel. Alternatively, any portion of the elastic member can consist of two or more elastic portions that are configured in parallel. In such configurations, the clutch mechanism can be configured to engage all of the elastic members (or portions) in parallel to get a higher stiffness, or just some subset of these to get an intermediate stiffness. In this way, the clutching mechanism can support variable levels of spring assistance for different tasks.

As noted above, engaging or disengaging assistance can be triggered manually. For example, in some embodiments, an accelerometer, tactile sensor, a button, or other control mechanism on wearable assistance device can be activated by the user. Alternatively, or additionally, assistance can also be triggered by activating a control on a wearer's smart phone, smart watch, or other computing device communicatively coupled to the processor.

Additionally, or alternatively, electromyography (EMG) sensors can be integrated into the wearable assistance device along with an automated algorithm that identifies when to engage or disengage assistance based on sensor data. However, in some embodiments, an external sensor can be used. For example, referring back to FIG. 6A, an EMG sensor 614 can be placed on the user's body. The EMG sensor 614 can be communicatively coupled with the processor 610. The processor 610 can then, based on an automated algorithm, determine if assistance is required for a user's current activities. For example, when utilizing EMG control, the processor 610 can identify when a wearer might want active assistance instead of passive assistance based on the EMG signal received from the control. The EMG control can transmit data on the wearer's EMG signals to the processor. The processor can engage or disengage the clutch based on the wearer's EMG signal. A rising or higher EMG signal indicates that the clutch should be engaged while a decreasing or lower EMG signal indicates that the clutch can be disengaged.

In addition, or as an alternative to EMG signals, other body dynamic data can be used in the various embodiments. For example, force or pressure sensors on the user's body can be used to generate signals indicating when assistance is required. Thus, pressure or force sensors can be activated during certain types of activities requiring assistance and the corresponding signals can be used to engage the clutch.

Figure 8:
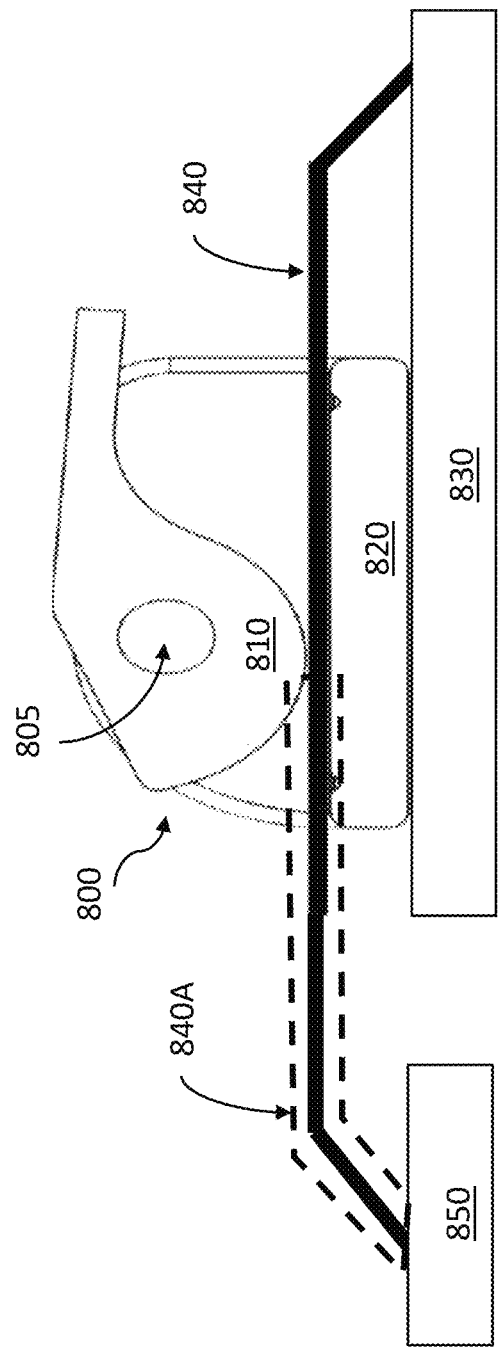
FIG. 8 shows a side perspective view illustration of a spring-loaded cam mechanism for clutching according to an embodiment of the invention.

The clutch mechanism itself can be implemented in a variety of ways. One configuration in accordance with the various embodiments is illustrated in FIG. 8. In particular, FIG. 8 shows a side perspective view of a clutch mechanism 800 which includes a friction cam 810 and a base 820. The clutch mechanism 800 can be attached to the upper-body interface 830 and a portion of elastic member 840 is fed between the friction cam 810 and the base 820. The elastic member 840 can be attached to the upper-body interface 830 on one end and to the lower-body interface 850 on the other end.

As shown in FIG. 8, the friction cam 810 and the base 820 are connected via a rotation hinge joint 805. When the friction cam 810 is disengaged, it is rotated upwards such that the friction cam 810 loses contact with the portion of elastic member 840. As a result, the elastic member 840 can then slide freely through the clutch mechanism 800. Consequently, forces are transferred between the upper-body interface 830 and the lower-body interface 850 along the entirety of the elastic member 840. Thus, as discussed above with respect to FIG. 7B, little or no assistance is provided.

When the friction cam 810 is engaged, it contacts the portion of elastic member 840 being fed through the friction cam 810 and this portion is rendered immobile. Consequently, when the friction cam 810 is engaged, the friction cam 810 and the base 820 cause forces from upper-body interface 830 to be transferred only along a lower portion 840A of the elastic member. Thus, as discussed above with respect to FIG. 7C, assistance is provided.

To operate a clutch mechanism in the various embodiments, an actuator can be provided. Such an actuator can be implemented in a variety of ways. In an exemplary embodiment, the actuator can be a small electric servomotor and battery located in a front pocket of the upper-body interface. A Bowden cable can be looped from the front pocket, over the shoulder to the wearer's mid-back, where a friction cam is located. When the motor is operated, the Bowden cable transmits motor motion into motion along the cable, which causes the clutch to engage or disengage. In other embodiments, the Bowden cable alternatively could go between the clutch and an actuator in any other method. The actuator alternatively can be located anywhere else on the wearable assistance device besides in a front pocket of the upper-body interface. However, actuation of the clutch mechanism is not limited to Bowden cables. Rather, any mechanism for engaging or disengaging a clutch mechanism can be used in the various embodiments.

Figure 9:
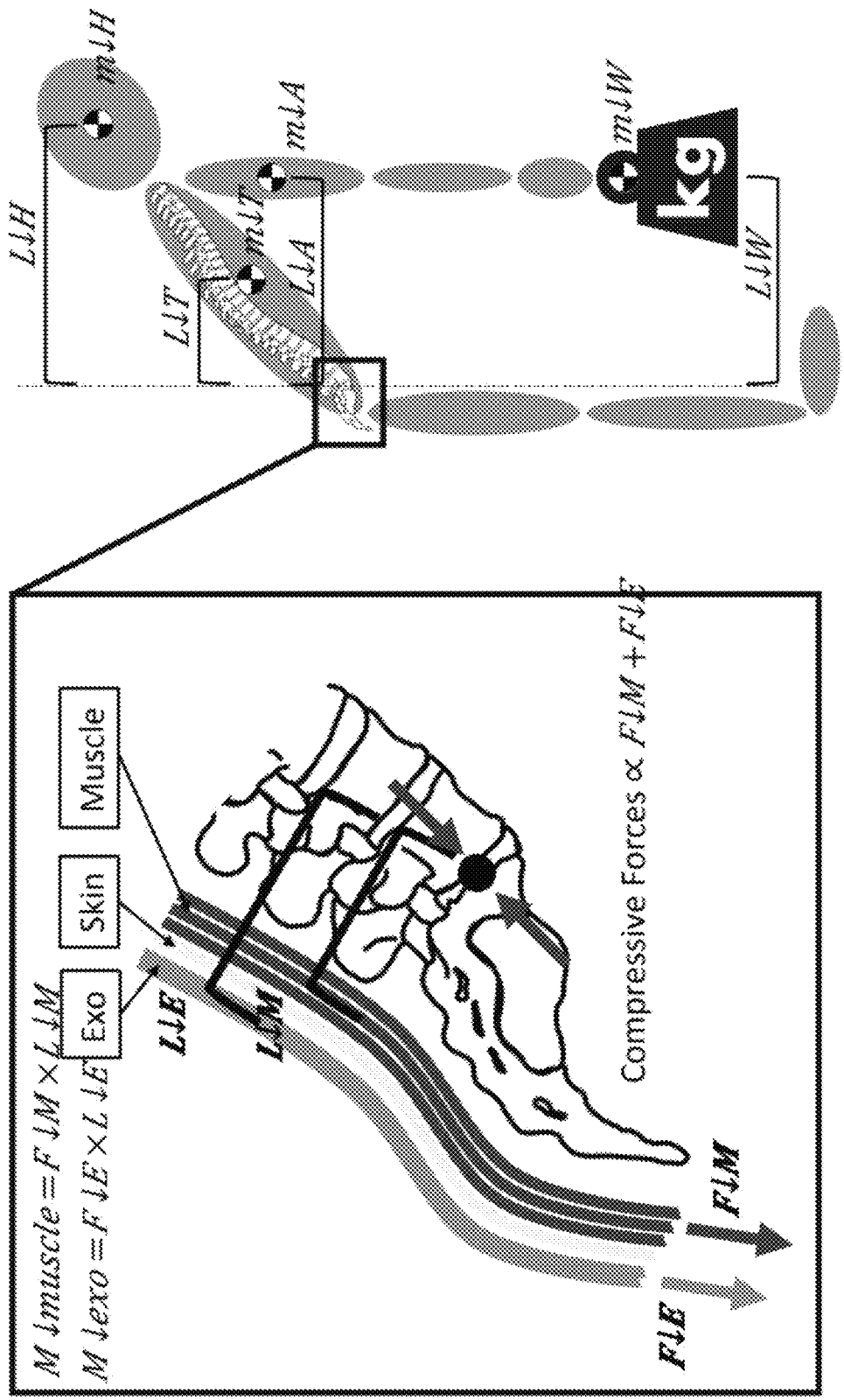
FIG. 9 illustrates the mechanical analysis of how a wearable assistance device reduces lower back stress.

FIG. 9 is an anatomical diagram illustrating the reduction in compressive forces when a wearable assistance device in accordance with the various embodiments is used. When an assistance device is used, both the assistance device and the lower back muscles contribute to a downward force against the lumbar spine. The compressive force must equal the sum of the muscle force and the assistance device force. This can be contrasted with FIG. 3 where the muscle force had to entirely respond to the compressive force. Referring back to FIG. 9, the counterbalancing muscle moment equals the cross product of compressive forces ($F \downarrow M$) and the distance from the lumbar spine moment to the center of mass for the person and the carried load ($L \downarrow M$). The assistance device moment equals the cross product of compressive forces of the assistance device and the distance from the assistance device to the person's center of mass. If the low back extensor moment was provided entirely by muscle, then the resultant compressive force on the spinal disc would be larger than if the moment resulted in part or in whole by the wearable assistance device. This is a mechanical consequence of the spring provided by the assistance device having a larger moment arm about the lumbar spine than the muscles.

Results with Wearable Assistance Device

Figure 10B:
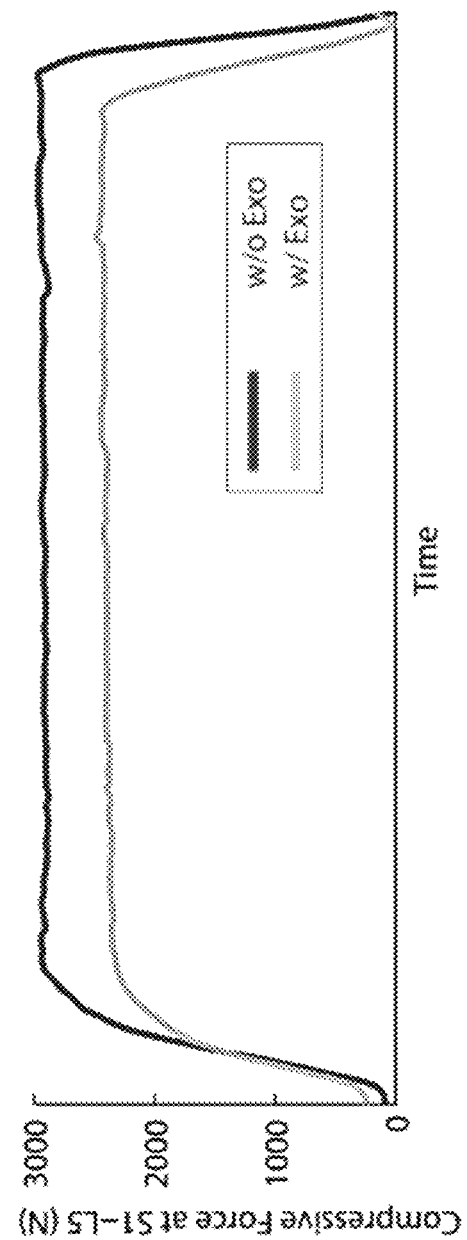
FIG. 10B is an X-Y plot of the compressive forces on a user's spine over time when wearing a wearable assistance device according to an embodiment of the invention as compared to when not using any assistance device.

FIG. 10A and FIG. 10B show how a wearable assistance device according to the various embodiments reduces muscular effort and spinal compression. FIG. 10A measures the EMG activity of a wearer while the wearer is wearing a wearable assistance device according to the various embodiments ("w/Exo") as compared to when the wearer is not wearing such a device ("w/o Exo"). As seen in FIG. 10A, the wearer's EMG activity is lower with a wearable assistance device according to the various embodiments. This shows that the wearer has reduced muscular effort when wearing the wearable assistance device according to the various embodiments as opposed to without it.

FIG. 10B estimates the compressive force acting on the S1 and L5 vertebrae in the wearer's spine. As shown by the XY-plot, the compressive forces acting on the S1 and L5 vertebrae are estimated to be lower with the wearable assistance device ("w/Exo") as opposed to without it ("w/o Exo"). This shows that the wearer has reduced spine compression when wearing a wearable assistance device according to the various embodiments as opposed to without it.

Figure 11A:
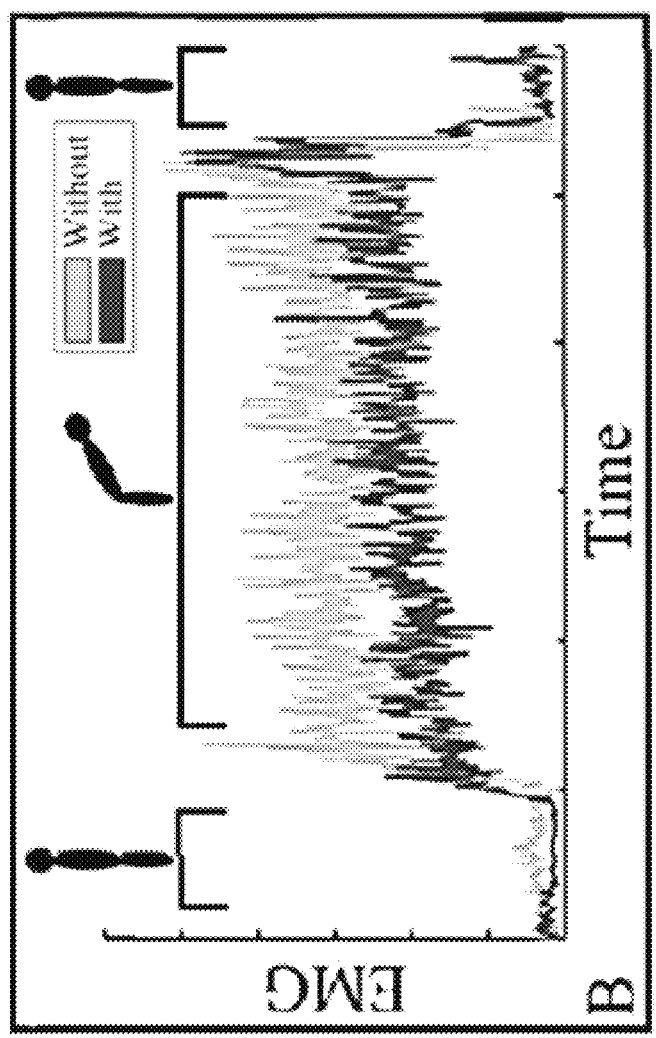
FIG. 11A is an X-Y plot of EMG activity for a user when leaning at a fixed angle when wearing a wearable assistance device according to an embodiment of the invention as compared to when not using any assistance device.

FIG. 11A shows the effects with a wearable assistance device according to the various embodiments ("With") and without such a device ("Without") during leaning and lifting tasks reduced EMG activity in the erector spinae. Mean EMG activity was collected from testing seven healthy subjects performing leaning and lifting tasks with and without a wearable assistance device according to the various embodiments. Subjects leaned forward at pre-determined angles while holding a 4.5 kilogram (kg) weight to their sternum. Mean EMG activity was computed by averaging the left and right erector spinae EMG and calculating an averaged time series signal over the middle 20 seconds of the trial in which the subjects were statically leaning.

Mean EMG activity across the participants was reduced by 15%±19% when leaning at a 30-degree angle, reduced by 27%±10% when leaning at a 60-degree angle, and reduced by 43%±33% when leaning at a 90-degree angle. These EMG reductions suggest that the wearable assistance device according to the various embodiments reduced lumbar muscle forces. Because lumbar muscle forces constitute the majority of compressive forces on the lumbar spine, a wearable assistance device according to the various embodiments should also reduce lumbar muscle and disc loading. This reduction in loading should help mitigate overuse and/or overloading risks that can lead to lower back injury and pain.

Figure 11B:
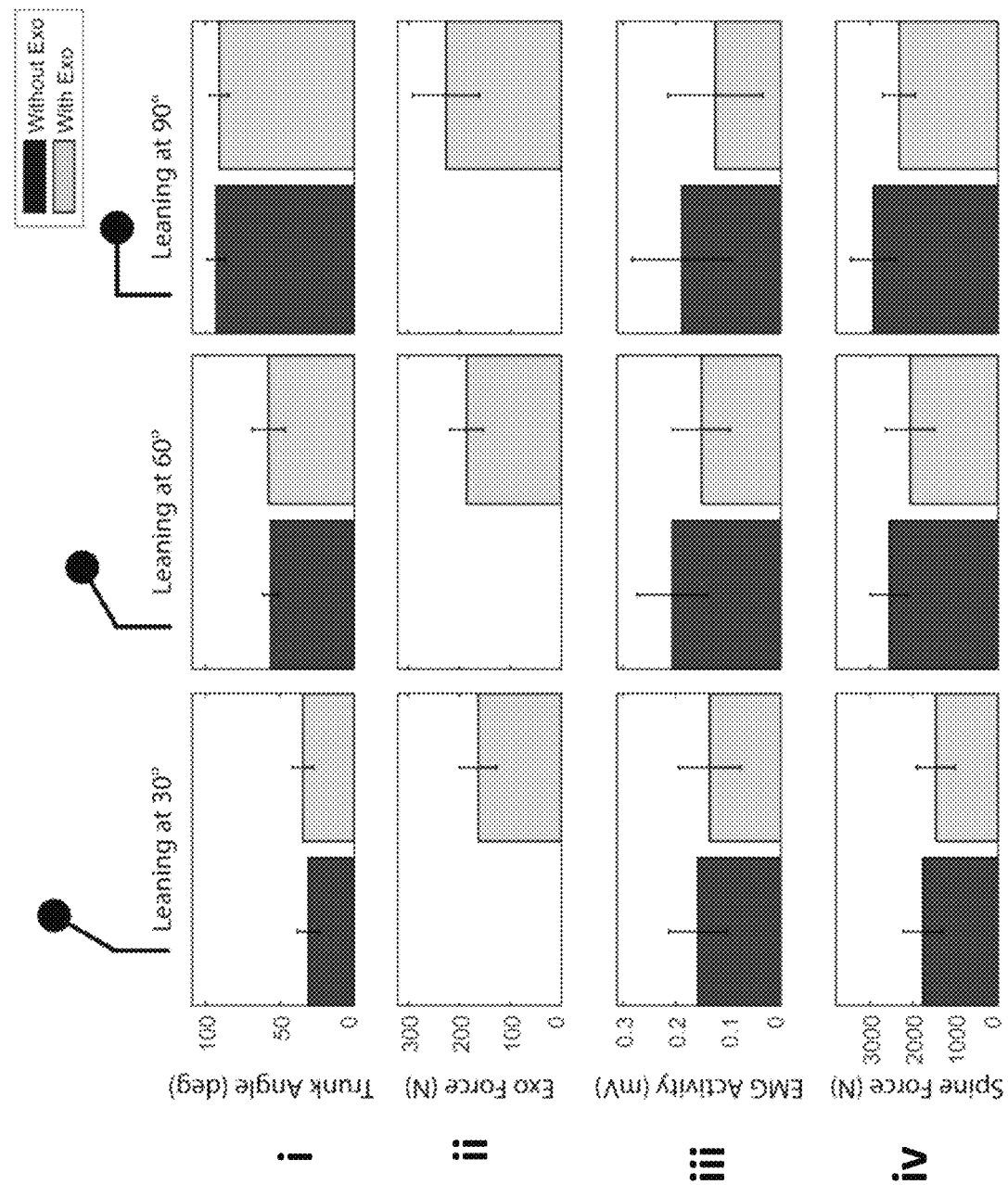
FIG. 11B shows effects of an embodiment of the invention for different forward leaning angles of a user.

FIG. 11B shows the amount of support provided with a wearable assistance device according to the various embodiments ("With Exo") and without such a device ("Without Exo"). The trunk angle graphs (row i) show what angle the wearer is leaning at when each set of data is measured. The Exo Force graphs (row ii) show the amount of force a wearable assistance device according to the various embodiments provides when leaning at various angles. The EMG activity graphs (row iii) shows that the wearer has greater EMG activity when not wearing the wearable assistance device according to the various embodiments. The Spine Force graphs in (row iv) show that at the three measured leaning angles of 30-degrees, 60-degrees, and 90-degrees, the wearer was estimated to incur a greater spine force when not wearing a wearable assistance device according to the various embodiments.

Figure 11C:
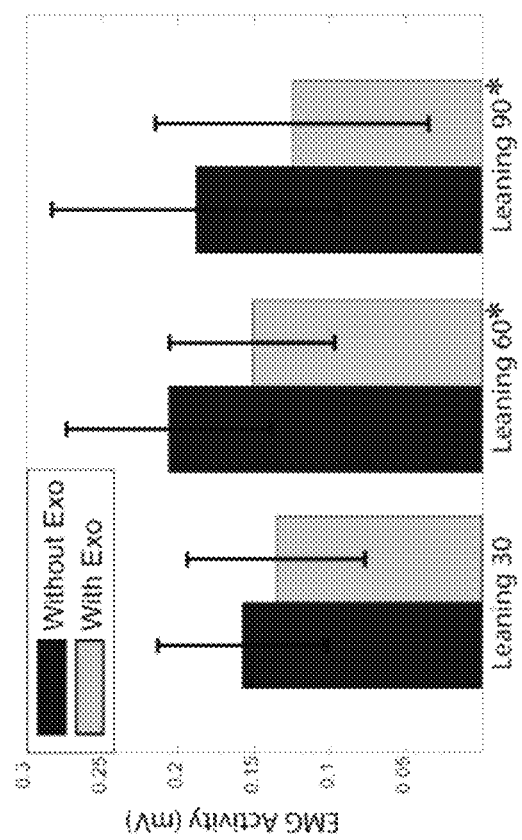
FIG. 11C shows the lower EMG activity while using a wearable assistance device according to an embodiment of the invention as compared to not using any assistance device.

FIG. 11C shows EMG activity for leaning at 30-degrees, 60-degrees, and 90-degrees with a wearable assistance device according to the various embodiments ("With Exo") and without such a device ("Without Exo"). EMG activity was collected from testing seven healthy subjects performing leaning and lifting tasks with and without a wearable assistance device according to the various embodiments. Subjects leaned forward at pre-determined angles while holding a 4.5 kg weight to their sternum. The graph shows the effectiveness of a wearable assistance device according to the various embodiments because at every leaning angle, wearers have lower EMG activity when wearing the wearable assistance device.

FIG. 12 shows the average erector spinae EMG activity for an individual during lifting of a 28 lb weight versus time (normalized to 1000 data points to represent lifting cycle). The results show reduced EMG activity of the low back muscles while using a wearable assistance device ("with exo") according to an embodiment of the invention as compared to not using any assistance device ("without exo").

FIG. 13 shows the average erector spinae EMG activity for an individual during lifting of a 53 lb weight versus time (normalized to 1000 data points to represent lifting cycle). The results show reduced EMG activity of the low back muscles while using a wearable assistance device ("with exo") according to an embodiment of the invention as compared to not using any assistance device ("without exo").

FIG. 14A measures EMG activity for a particular wearer, Subject 1, at a static leaning task of an angle between 45 and 60 degrees. Subject 1 has a lower EMG percent envelope with a mean at 0.16239 when wearing a wearable assistance device according to the various embodiments ("w/Exo"). Without a wearable assistance device according to the various embodiments ("w/o Exo"), the same wearer has a EMG percent envelope with a mean at 0.28213. This discrepancy shows that the wearer exerts less effort when wearing a wearable assistance device according to the various embodiments.

FIG. 14B shows the moment for the L5 and S1 vertebrae during the same leaning task. This graph shows that a wearer with a wearable assistance device according to the various embodiments ("w/Exo") has a greater moment than without a wearable assistance device ("w/o Exo"). This shows the effectiveness of a wearable assistance device according to the various embodiments because a higher moment means that the wearer has to exert less force when leaning.

FIG. 15A shows the EMG percent envelope for a second subject at a static leaning task of between 45 and 60 degrees. Subject 2 has a lower EMG percent envelope with a mean at 0.17585 when wearing a wearable assistance device according to the various embodiments ("w/Exo"). Without the wearable assistance device according to the various embodiments, the same wearer has a EMG percent envelope mean at 0.27304 ("w/o Exo"). This discrepancy shows that the wearer exerts less effort when wearing the wearable assistance device according to the various embodiments.

FIG. 15B shows the moment for Subject 2's L5 and S1 vertebrae during the same leaning task. This graph shows that a wearer with a wearable assistance device according to the various embodiments ("w/Exo") has a greater moment than without a wearable assistance device ("w/o Exo"). This shows the effectiveness of the wearable assistance device because a higher moment means that the wearer has to exert less force when leaning.

FIG. 16A shows the EMG percent envelope for a first subject at a static leaning task of 90 degrees. Subject 1 has a lower EMG percent envelope with a mean at 0.15157 when wearing a wearable assistance device according to the various embodiments ("w/Exo"). Without the wearable assistance device according to the various embodiments, the same wearer has a EMG percent envelope mean at 0.35147 ("w/o Exo"). This discrepancy shows that the wearer exerts less effort when wearing the wearable assistance device according to the various embodiments.

FIG. 16B shows the moment for Subject 1's L5 and S1 vertebrae during the same leaning task. This graph shows that a wearer with a wearable assistance device according to the various embodiments ("w/Exo") has a greater moment than without a wearable assistance device ("w/o Exo"). This shows the effectiveness of the wearable assistance device according to the various embodiments because a higher moment means that the wearer has to exert less force when leaning.

FIG. 17A shows the EMG percent envelope for a second subject at a static leaning task of 90 degrees. Subject 2 has a lower EMG percent with a mean at 0.20274 when wearing a wearable assistance device according to the various embodiments ("w/Exo"). Without the wearable assistance device according to the various embodiments, the same wearer has a EMG percent envelope at 0.31649 ("w/o Exo"). This discrepancy shows that the wearer exerts less effort when wearing the wearable assistance device according to the various embodiments.

FIG. 17B shows the moment for Subject 2's L5 and S1 vertebrae during the same leaning task. This graph has almost identical moments regardless of whether Subject 2 is wearing a wearable assistance device according to the various embodiments ("w/Exo") or not ("w/o Exo"). Although this may appear to be inconclusive as to the effect on the wearer, FIG. 17A shows that although Subject 2 has similar moments, Subject 2 still exerts lower effort when wearing a wearable assistance device according to the various embodiments.

FIG. 18 shows the EMG activity of the lower back erector spinae muscles during lifting activity averaged over data collected from eight healthy subjects with and without a wearable assistance device according to the various embodiments. Lifting trials were parsed into cycles, where a cycle begins with the subject standing upright. The cycle is at 50% when the subject is at the bottom of the lift, and at 100% when the subject is standing upright again. Average lift cycle durations were calculated to ensure that cycle durations remained consistent for different weights.

FIG. 18 also shows that when a wearer has a wearable assistance device according to the various embodiments, the EMG activity of the erector spinae muscles is lower during periods of high activity than when the wearer does not have a wearable assistance device according to the various embodiments. This suggests that a wearable assistance device according to the various embodiments is successful at reducing strain on reducing on lower back muscles.

FIG. 19 shows compression force in kilonewtons (kN) during a lift cycle. This was estimated with a simple spine model and paired t-tests to compare the disc loading with or without wearable assistance device according to the various embodiments. FIG. 19 shows how a wearer with a wearable assistance device according to the various embodiments has a lower compressive force during the majority of the lift cycle than a wearer would have without such a wearable assistance device.

FIGS. 20A and 20B shows analysis of mean and peak EMG activity, respectively, for different lifting tasks to compare activity with a wearable assistance device according to the various embodiments versus activity without a wearable assistance device. FIG. 20C shows analysis of mean EMG activity for different leaning tasks to compare activity with a wearable assistance device according to the various embodiments versus activity without a wearable assistance device. This data was collected from eight healthy subjects while wearing and not wearing a wearable assistance device according to the various embodiments. By all measures, whether lifting tasks of different weights or leaning tasks of different angles, the wearer has lower EMG activity when wearing a wearable assistance device according to the various embodiments. This provides broad support for the use of wearable assistance device according to the various embodiments to reduce lower back fatigue.

ADDITIONAL EMBODIMENTS

Lower Body Interface

In the various embodiments, a wide variety of materials can be used to form the upper and lower-body interfaces of the wearable assistant device discussed above. Conventional exoskeletons are made with rigid materials and hard, bulky exteriors. Additionally, many conventional exoskeletons adhere to the person through straps or hard plastic interfaces. This can cause bruising or soft tissue damage to the body area under the straps. This is especially true for the lower-body interface.

In view of such limitations, in some embodiments, the sleeves defining the lower-body interface can be made from thermoplastic elastomer or silicon and can be custom designed to fit the wearer's exact body type. The sleeve could also be made of a stretchable material to fit wearers of different sizes. On top of the sleeve can be a semi-rigid or non-rigid fabric cover. The cover attaches to other components of the wearable assistance device while the sleeve functions primarily to protect the wearer's skin and help distribute pressure evenly. Such a configuration is illustrated in FIG. 21.

In some embodiments, as illustrated in FIG. 22, the sleeve of the wearable assistance device can be a thermoplastic elastomer/silicone sleeve with a compressive fabric cover. The compressive fabric cover can have one-way stretch or can have selectively stiff portions that are configured to distribute weight evenly. FIG. 22 illustrates the wearable assistance device with the upper-body interface 602, the lower-body interface 604, the one or more elastic members 606 that each has a first portion 606A and a second portion 606B, and a clutch 608 with an actuator 611.

FIG. 23 shows how the thermoplastic elastomer/silicone sleeve and compressive fabric cover is configured. The sleeve conforms around the limb segment and grips the skin to prevent the sleeve from slipping into a different configuration on the limb. In this example, the sleeve grips the wearer's legs. A fabric cover attaches on top of the sleeve and can be attached to the sleeve via Velcro or other means. Elastic bands can attach to the fabric cover. External force from the exo-elastic bands can then be applied to the outer cover. The combination of the fabric cover and the thermoplastic elastomer/silicone sleeve allows force from the elastic bands to distribute over the surface area of skin so that large forces can be applied without the sleeve slipping from the limb.

FIG. 24 shows how much displacement different configurations of a lower-body interface provide depending on the force applied. With just a standard strap or shell without the sleeve and cover as disclosed in FIG. 21 through FIG. 23, the interface will move too much to be operable and effectively fail at approximately 300 N. This is shown by curve 2402 in FIG. 24. An exo-interface with the cover/liner only can withstand much higher forces than the standard strap/shell, as shown by curve 2404. An exo-interface with both a liner and a skin adhesive such as the thermoplastic elastomer/silicone sleeve discussed above, can withstand force with even less displacement than the exo-interface with just a liner, as shown by curve 2406. Therefore, FIG. 24 shows that a wearable assistance device according to the various embodiments can be configured to can support loads over twice as heavy as the standard strap/shell attachments.

Assistance of Other Joints

Other embodiments can be constructed to assist other joints. For example, upper and lower interfaces of a wearable assistance device according to some embodiments could be coupled between the wearer's trunk and the wearer's head. This coupling can offload the neck such as to assist a surgeon whose head is tilted forward for long periods during an operation. Upper and lower interfaces of a wearable assistance device according to some embodiments can be coupled between the upper and lower arms to offload the bicep muscles. This can be useful for a parent who carries a child on their arm for an extended period of time. Coupling between the shank and the foot can provide assistance to individuals with weak calf muscles. Elastic assistance can be selectively engaged or disengaged with the same clutching mechanism.

Integration Into Clothing

FIG. 25 shows how the principles discussed herein can be integrated into every day clothing. For example, a shirt could have embedded elastic which resists movement during lifting and leaning tasks. The shoulder area of the shirt could have tension adjustability or a clutching mechanism that is easily accessible to the wearer. Both the shirt and the pants of can be made from breathable non-slip garments to allow for force to be distributed across the wearer's body.

Side to Side Differential

In some embodiments, the wearable assistance devices described herein can be designed with a side-to-side differential. When a wearer leans to the right, or forward and partially to the right, the lower left muscles of the back undergo higher strain than muscles on the right side. An wearable assistance devices can be designed to naturally accommodate asymmetry to provide support to each side of the lower back when leaning right or left. This side-to-side differential can be achieved by crisscrossing the elastic cables along the back. The side-to-side differential could also be achieved by adding elastic members along the left and right sides of the user. Side-to-side differential could also be added via other means such as integrating a small pulley or lever mechanism between elastic members.

Resistance Applications

In some embodiments, the wearable assistance devices described herein can be used to train the abdominal muscles where a wearable assistance device according to the various embodiments could be selectively engaged to resist forward bending movement. When the wearer attempts to lean forward, the stiff elastic member(s) running along the back could be engaged. Users would need to exert sufficient abdominal muscle effort to bend normally plus the additional effort needed to stretch the elastic band. In this way the wearer's abdominal muscles would get an increased workout to help strengthen the person's core. In some configurations, a viscous or viscoelastic member can be used.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A wearable lower back assistance device configured to be worn by a user, comprising:
    an upper-body interface;
    a lower-body interface;
    one or more elastic members, each of the elastic members mechanically coupling the upper-body interface to the lower-body interface and extending from the upper-body interface to the lower-body interface and configured along a back of the user so as to provide an assistive force parallel to the back of the user, and configured to curve about a portion of a user's buttocks when the user bends forward;
    a clutch mechanism associated with each one of the elastic members, wherein the clutch mechanism is configured for selectively adjusting the assistive force by changing a load path between the upper-body interface and the lower-body interface through one or more of the elastic members, when the clutch mechanism changes from disengaged to engaged; and
    an actuator associated with the clutch mechanism for engaging and disengaging the clutch mechanism, and the actuator being located on a front of the upper-body interface,
    wherein the upper-body interface is a garment top configured to cover at least a portion of shoulders of the user, and wherein the clutch mechanism is mechanically connected to the garment top.

2. The assistance device of claim 1, wherein each of the elastic members comprises a first portion and a second portion connected in series, wherein the first portion is connected to the upper-body interface, wherein the second portion is connected to the lower-body interface, each of the first portion and the second portion having a different stiffness.

3. The assistance device of claim 2, wherein the stiffness of the second portion is greater than the stiffness of the first portion.

4. The assistance device of claim 3, wherein the clutch mechanism is positioned between the first portion and the second portion.

5. The assistance device of claim 1, further comprising a processor configured for controlling an operation of the clutch mechanism.

6. The assistance device of claim 5, further comprising at least one electromyography sensor communicatively coupled to the processor, and wherein the processor controls the operation of the clutch mechanism based on an output signal from the at least one electromyography sensor.

7. The assistance device of claim 5, wherein the processor is further configured for receiving body dynamics data and adjusting the operation of the clutch mechanism based on the body dynamics data.

8. The assistance device of claim 5, wherein the actuator is an electric motor that is controlled by the processor to adjust the operation of the clutch mechanism.

9. The assistance device of claim 1, wherein each of the one or more elastic members comprises a first portion and a second portion connected in series, and wherein the first portion is connected to the upper-body interface, and the second portion is connected to the lower-body interface.

10. The assistance device of claim 9, wherein the clutch mechanism sets the load path through one of the following first load paths:
    A) the first portion and second portion of each elastic member;
    B) the first portion of each elastic member; or
    C) the second portion of each elastic member,
    when the clutch mechanism is engaged; and
    wherein the clutch mechanism sets the load path through a second load path different than the first load path, when the clutch mechanism is disengaged.

11. The assistance device of claim 1, wherein a mechanical connection extends between the actuator and the clutch mechanism.

12. The assistance device of claim 11, wherein the mechanical connection is a Bowden cable.

13. The assistance device of claim 1, wherein the actuator is a button or other mechanism that can be triggered manually to adjust the operation of the clutch mechanism.

14. The assistance device of claim 1, wherein the upper-body interface is in the form of a vest.

15. The assistance device of claim 1, wherein the lower-body interface is in the form of leg sleeves or shorts.

16. The assistance device of claim 1, wherein the one or more elastic members comprise:
    a first elastic member extending from a right side of the upper-body interface to a left side of the lower-body interface; and
    a second elastic member extending from a left side of the upper-body interface to a right side of the lower-body interface.

17. The assistance device of claim 1, wherein the clutch mechanism comprises a rotating cam that fixates or clamps the one or more elastic members when the clutch mechanism is engaged.

18. A method for operating a wearable assistance device having an upper-body interface, a lower-body interface, one or more elastic members coupling the upper-body interface to the lower-body interface and extending from the upper-body interface to the lower-body interface and along a back of the user so as to provide an assistive force parallel to the back of the user, the one or more elastic members curving about a portion of a user's buttocks when the user bends forward, a clutch mechanism associated with each one of the elastic members, and an actuator associated with the clutch mechanism for engaging and disengaging the clutch mechanism, the actuator being located on a front of the upper-body interface and wherein the upper-body interface is a garment top configured to cover at least a portion of shoulders of the user, and wherein the clutch mechanism is mechanically connected to the garment top, the method comprising:

determining, via a processor, whether a current activity of the user requires assistive force; and upon determining that the current activity requires assistive force, generating, via the processor, control signals for the clutch mechanism that cause the clutch mechanism to increase the assistive force provided via an associated one of the elastic members, by changing a load path between the upper-body interface and the lower-body interface through the one or more of the elastic members, when the clutch mechanism changes from disengaged to engaged.

19. The method of claim 18, wherein determining whether a current activity of the user requires assistive force further comprises:

receiving electromyogram (EMG) signals associated with the user;

identifying a trend in the EMG signals; and ascertaining whether the current activity requires assistive force based on the trend.

20. The method of claim 19, wherein the current activity is ascertained to require assistive force is the trend in the EMG signals is increasing.

21. The method of claim 19, wherein the current activity is ascertained to not require assistive force is the trend in the EMG signals is decreasing.

22. The method of claim 18, wherein each of the one or more elastic members comprises a first portion and a second portion connected in series, wherein the first portion is connected to the upper-body interface, and the second portion is connected to the lower-body interface.

23. The method of claim 22, wherein the clutch mechanism sets the load path through one of the following first load paths:

A) the first portion and second portion of each elastic member;

B) the first portion of each elastic member; or

C) the second portion of each elastic member, when the clutch mechanism is engaged; and wherein the clutch mechanism sets the load path through a second load path different than the first load path, when the clutch mechanism is disengaged.

24. The method of claim 18, further comprising:

upon determining that the current activity requires no assistive force, generating, via the processor, control signals for the clutch mechanism, the control signals configured to decrease the assistive force provided via an associated one of the elastic members.

25. The method of claim 18, wherein determining whether a current activity of the user requires assistive force further comprises:

receiving, via the processor, body dynamics data for the user; and ascertaining whether the current activity requires assistive force based on the body dynamics data.

26. The method of claim 18, wherein the clutch mechanism comprises a rotating cam that fixates or clamps the one or more elastic members when the clutch mechanism is engaged.

27. The method of claim 18, wherein the actuator is a button or other mechanism that can be triggered manually to adjust the operation of the clutch mechanism.

28. The method of claim 18, wherein the actuator is an electric motor that is controlled by the processor to adjust the operation of the clutch mechanism.

29. A wearable lower back assistance device configured to be worn by a user, comprising:

an upper-body interface;

a lower-body interface;

at least one elastic member comprising at least a first portion connected to the upper-body interface and a second portion connected the lower-body interface, respectively, the first portion and the second portion of the at least one elastic member having different stiffnesses;

at least one clutch mechanism coupled to the at least one elastic member between the first and second portions thereof; and an actuator associated with the clutch mechanism for engaging and disengaging the clutch mechanism, and the actuator being located on a front of the upper-body interface, wherein the at least one elastic member mechanically couples the upper-body interface to the lower-body interface, thereby providing an assistive force to the back of the user, and the clutch mechanism is configured for selectively adjusting the assistive force by changing a load path between the upper-body interface and the lower-body interface, through the at least one elastic member, when the clutch mechanism changes from disengaged to engaged, and wherein the upper-body interface is a garment top configured to cover at least a portion of shoulders of the user, and the at least one clutch mechanism is coupled to the garment top.

30. The assistance device of claim 29, wherein a mechanical connection extends between the actuator and the clutch mechanism.

31. The assistance device of claim 30, wherein the mechanical connection is a Bowden cable.

32. The assistance device of claim 29, wherein the actuator is a button or other mechanism that can be triggered manually to adjust the operation of the clutch mechanism.

33. The assistance device of claim 29, wherein the actuator is an electric motor that is controlled by the processor to adjust the operation of the clutch mechanism.

\* \* \* \* \*

UNITED STATES PATENT AND TRADEMARK OFFICE
CERTIFICATE OF CORRECTION

| | | |
|---|---|---|
| PATENT NO. | : 11,980,563 B2 | Page 1 of 1 |
| APPLICATION NO. | : 16/478310 | |
| DATED | : May 14, 2024 | |
| INVENTOR(S) | : Zelik et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this
Thirty-first Day of December, 2024

Derrick Brent
*Acting Director of the United States Patent and Trademark Office*